(12) United States Patent
Gerlach et al.

(10) Patent No.: US 7,905,910 B2
(45) Date of Patent: *Mar. 15, 2011

(54) BONE PLATES AND BONE PLATE ASSEMBLIES

(75) Inventors: Darin Gerlach, Cordova, TN (US); Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1 day.

This patent is subject to a terminal disclaimer.

(21) Appl. No.: 11/644,306

(22) Filed: Dec. 22, 2006

(65) Prior Publication Data

US 2007/0162020 A1    Jul. 12, 2007

Related U.S. Application Data

(63) Continuation of application No. 10/673,833, filed on Sep. 29, 2003, now Pat. No. 7,179,260.

(51) Int. Cl.
*A61B 17/80* (2006.01)

(52) U.S. Cl. .......................................... 606/291; 606/915

(58) Field of Classification Search .................. 606/280, 606/281, 282, 286, 291, 70, 71, 915, 86 B
See application file for complete search history.

(56) References Cited

U.S. PATENT DOCUMENTS

| | | | |
|---|---|---|---|
| 575,631 A | 1/1897 | Brooks | |
| 902,040 A | 10/1908 | Wyckoff | |
| 2,501,978 A | 3/1950 | Wichman | |
| 2,699,774 A | 1/1955 | Livingston | |
| 3,530,854 A | 9/1970 | Kearney | |
| 3,866,607 A | 2/1975 | Forsythe et al. | |
| RE28,841 E | 6/1976 | Allgower et al. | |
| 4,388,921 A | 6/1983 | Sutter et al. | |
| 4,408,601 A | 10/1983 | Wenk | |
| RE31,628 E | 7/1984 | Allgower et al. | |
| 4,484,570 A | 11/1984 | Sutter et al. | |
| 4,565,193 A | 1/1986 | Streli | |
| 4,622,959 A | 11/1986 | Marcus | |
| 4,657,001 A | 4/1987 | Fixel | |
| 4,836,196 A | 6/1989 | Park et al. | |
| 4,838,252 A | 6/1989 | Klaue | |
| 4,927,421 A | 5/1990 | Goble et al. | |
| 4,988,350 A | 1/1991 | Herzberg | |
| 5,002,544 A | 3/1991 | Klaue et al. | |
| 5,013,313 A | 5/1991 | Surer | |
| 5,041,113 A | 8/1991 | Biedermann et al. | |

(Continued)

FOREIGN PATENT DOCUMENTS

DE    43 43 117 A1    6/1995

(Continued)

OTHER PUBLICATIONS

Brochure entitled Introducing Peak™ Polyaxial Anterior Cervical Plate, by Depuy Motech, one page, undated.

(Continued)

*Primary Examiner* — Pedro Philogene

(74) *Attorney, Agent, or Firm* — Fish & Richardson P.C.

(57) ABSTRACT

Bone plates with an upper surface, a bone contacting surface, and at least one hole extending through the upper and bone contact surfaces are disclosed. A hole interchangeably accepts a compression screw for compression of a fracture and a locking screw that threads into the bone plate.

18 Claims, 15 Drawing Sheets

U.S. PATENT DOCUMENTS

| | | | |
|---|---|---|---|
| 5,041,114 A | 8/1991 | Chapman et al. | |
| 5,041,116 A | 8/1991 | Wilson | |
| 5,053,036 A | 10/1991 | Perren et al. | |
| 5,057,111 A | 10/1991 | Park | |
| 5,085,660 A | 2/1992 | Lin | |
| 5,127,914 A | 7/1992 | Calderale et al. | |
| 5,129,901 A | 7/1992 | Decoste | |
| 5,151,103 A | 9/1992 | Tepic et al. | |
| 5,190,544 A | 3/1993 | Chapman et al. | |
| 5,197,966 A | 3/1993 | Sommerkamp | |
| 5,261,910 A | 11/1993 | Warden et al. | |
| 5,269,784 A | 12/1993 | Mast | |
| 5,275,601 A | 1/1994 | Gogolewski et al. | |
| 5,304,180 A | 4/1994 | Slocum | |
| 5,312,410 A | 5/1994 | Miller et al. | |
| 5,324,290 A | 6/1994 | Zdeblick et al. | |
| 5,324,291 A | 6/1994 | Ries et al. | |
| 5,364,398 A | 11/1994 | Chapman et al. | |
| 5,387,217 A | 2/1995 | Sefcik et al. | |
| 5,395,374 A | 3/1995 | Miller et al. | |
| 5,415,658 A | 5/1995 | Kipela et al. | |
| 5,423,820 A | 6/1995 | Miller et al. | |
| 5,429,641 A | 7/1995 | Gotfried | |
| 5,431,659 A | 7/1995 | Rose, Jr. et al. | |
| 5,470,333 A | 11/1995 | Ray | |
| 5,474,553 A | 12/1995 | Baumgart | |
| 5,486,176 A | 1/1996 | Hildebrand et al. | |
| 5,501,684 A | 3/1996 | Schlapfer et al. | |
| 5,520,690 A | 5/1996 | Errico et al. | |
| 5,527,310 A | 6/1996 | Cole et al. | |
| 5,536,127 A | 7/1996 | Pennig | |
| 5,549,612 A | 8/1996 | Yapp et al. | |
| 5,569,253 A | 10/1996 | Farris et al. | |
| 5,571,184 A | 11/1996 | DeSatnick | |
| 5,601,553 A | 2/1997 | Trebing et al. | |
| 5,607,428 A | 3/1997 | Lin | |
| 5,609,596 A | 3/1997 | Pepper | |
| 5,616,144 A | 4/1997 | Yapp et al. | |
| 5,665,088 A | 9/1997 | Gil et al. | |
| 5,676,666 A | 10/1997 | Oxland et al. | |
| 5,676,667 A | 10/1997 | Hausman | |
| 5,681,311 A | 10/1997 | Foley et al. | |
| 5,681,312 A | 10/1997 | Yuan et al. | |
| 5,702,399 A | 12/1997 | Kipela et al. | |
| 5,709,686 A | 1/1998 | Talos et al. | |
| 5,713,900 A | 2/1998 | Benzel et al. | |
| 5,713,902 A | 2/1998 | Friedl | |
| 5,735,853 A | 4/1998 | Olerud | |
| 5,741,256 A | 4/1998 | Bresina | |
| 5,741,258 A | 4/1998 | Kalue et al. | |
| 5,742,872 A | 4/1998 | Copperwheat et al. | |
| 5,772,662 A | 6/1998 | Chapman et al. | |
| 5,776,194 A | 7/1998 | Mikol et al. | |
| 5,788,697 A | 8/1998 | Kilpela et al. | |
| 5,797,911 A | 8/1998 | Sherman et al. | |
| 5,797,912 A | 8/1998 | Runciman et al. | |
| 5,800,433 A | 9/1998 | Benzel et al. | |
| 5,807,396 A | 9/1998 | Raveh | |
| 5,810,823 A | 9/1998 | Klaue et al. | |
| 5,836,950 A | 11/1998 | Hansson | |
| 5,843,082 A | 12/1998 | Yuan et al. | |
| 5,891,145 A | 4/1999 | Morrison et al. | |
| 5,893,856 A | 4/1999 | Jacob et al. | |
| 5,902,305 A | 5/1999 | Beger et al. | |
| 5,904,683 A | 5/1999 | Pohndorf et al. | |
| 5,935,130 A | 8/1999 | Kipela et al. | |
| 5,935,133 A | 8/1999 | Wagner et al. | |
| 5,935,169 A | 8/1999 | Chan | |
| 5,954,722 A | 9/1999 | Bono | |
| 5,957,953 A | 9/1999 | DiPoto et al. | |
| 5,961,521 A | 10/1999 | Roger | |
| 5,964,767 A | 10/1999 | Tapia et al. | |
| 5,964,769 A | 10/1999 | Wagner et al. | |
| 5,968,046 A | 10/1999 | Castleman | |
| 5,976,141 A | 11/1999 | Haag et al. | |
| 5,997,541 A | 12/1999 | Schenk | |
| 6,001,130 A | 12/1999 | Bryan et al. | |
| 6,017,345 A | 1/2000 | Richelsoph | |
| 6,022,350 A | 2/2000 | Ganem | |
| 6,022,352 A | 2/2000 | Vandewalle | |
| 6,030,389 A | 2/2000 | Wagner et al. | |
| 6,053,921 A | 4/2000 | Wagner et al. | |
| 6,096,040 A | 8/2000 | Esser | |
| 6,129,730 A | 10/2000 | Bono et al. | |
| 6,139,552 A | 10/2000 | Horiuchi | |
| 6,166,861 A | 12/2000 | Koizumi | |
| 6,176,861 B1 | 1/2001 | Bernstein et al. | |
| 6,193,721 B1 | 2/2001 | Michelson | |
| 6,206,881 B1 | 3/2001 | Frigg et al. | |
| 6,221,074 B1 | 4/2001 | Cole et al. | |
| 6,235,031 B1 | 5/2001 | Hodgeman et al. | |
| 6,235,033 B1 | 5/2001 | Brace et al. | |
| 6,306,136 B1 | 10/2001 | Baccelli | |
| 6,306,140 B1 | 10/2001 | Siddiqui | |
| 6,322,562 B1 * | 11/2001 | Wolter | 606/62 |
| 6,336,930 B1 | 1/2002 | Stalcup et al. | |
| 6,355,043 B1 | 3/2002 | Adam | |
| 6,358,250 B1 | 3/2002 | Orbay | |
| 6,361,537 B1 | 3/2002 | Anderson | |
| 6,364,882 B1 | 4/2002 | Orbay | |
| 6,364,885 B1 | 4/2002 | Kilpela et al. | |
| 6,391,030 B1 | 5/2002 | Wagner et al. | |
| 6,406,477 B1 | 6/2002 | Fujiwara | |
| 6,413,259 B1 | 7/2002 | Lyons et al. | |
| 6,423,066 B1 | 7/2002 | Harder et al. | |
| 6,428,542 B1 | 8/2002 | Michelson | |
| 6,440,135 B2 | 8/2002 | Orbay et al. | |
| 6,443,954 B1 | 9/2002 | Bramlet et al. | |
| 6,454,769 B2 | 9/2002 | Wagner et al. | |
| 6,475,218 B2 | 11/2002 | Gournay et al. | |
| 6,506,191 B1 | 1/2003 | Joos | |
| 6,520,965 B2 | 2/2003 | Chervitz et al. | |
| 6,595,994 B2 | 7/2003 | Kilpela et al. | |
| 6,623,486 B1 * | 9/2003 | Weaver et al. | 606/281 |
| 6,648,889 B2 | 11/2003 | Bramlet et al. | |
| 6,652,529 B2 | 11/2003 | Swanson | |
| 6,656,179 B1 | 12/2003 | Schaefer et al. | |
| 6,682,533 B1 | 1/2004 | Diinsdale et al. | |
| 6,730,091 B1 * | 5/2004 | Pfefferle et al. | 606/70 |
| 6,821,278 B2 * | 11/2004 | Frigg et al. | 606/291 |
| 6,960,213 B2 | 11/2005 | Chervitz et al. | |
| 7,052,499 B2 * | 5/2006 | Steger et al. | 606/291 |
| 7,137,987 B2 | 11/2006 | Patterson et al. | |
| 7,179,260 B2 * | 2/2007 | Gerlach et al. | 606/291 |
| 7,282,053 B2 | 10/2007 | Orbay | |
| 7,306,600 B2 | 12/2007 | Roth et al. | |
| 7,316,687 B2 | 1/2008 | Aikins et al. | |
| 7,341,589 B2 | 3/2008 | Weaver et al. | |
| 7,344,537 B1 | 3/2008 | Mueller | |
| 7,537,596 B2 | 5/2009 | Jensen | |
| 7,695,472 B2 | 4/2010 | Young | |
| 2001/0011172 A1 | 8/2001 | Orbay et al. | |
| 2001/0037112 A1 | 11/2001 | Brace et al. | |
| 2001/0047174 A1 | 11/2001 | Donno et al. | |
| 2002/0013587 A1 | 1/2002 | Winquist et al. | |
| 2002/0045896 A1 | 4/2002 | Michelson | |
| 2002/0045901 A1 | 4/2002 | Wagner et al. | |
| 2002/0049445 A1 | 4/2002 | Hall, IV et al. | |
| 2002/0058940 A1 | 5/2002 | Frigg et al. | |
| 2002/0058943 A1 | 5/2002 | Kilpela et al. | |
| 2002/0072753 A1 | 6/2002 | Cohen | |
| 2002/0143333 A1 | 10/2002 | von Hoffmann et al. | |
| 2002/0143338 A1 | 10/2002 | Orbay et al. | |
| 2002/0156473 A1 | 10/2002 | Branket et al. | |
| 2002/0156475 A1 | 10/2002 | Lerch et al. | |
| 2002/0161370 A1 | 10/2002 | Frigg et al. | |
| 2002/0183752 A1 | 12/2002 | Steiner et al. | |
| 2002/0183754 A1 | 12/2002 | Michelson | |
| 2002/0183755 A1 | 12/2002 | Michelson | |
| 2003/0018335 A1 | 1/2003 | Michelson | |
| 2003/0040749 A1 | 2/2003 | Grabowski et al. | |
| 2003/0040752 A1 | 2/2003 | Kitchens | |
| 2003/0060827 A1 | 3/2003 | Coughln | |
| 2003/0074000 A1 | 4/2003 | Roth et al. | |
| 2003/0078581 A1 | 4/2003 | Frei et al. | |
| 2003/0187440 A1 | 10/2003 | Richelsoph et al. | |
| 2003/0220641 A1 | 11/2003 | Thelen et al. | |

| | | | |
|---|---|---|---|
| 2004/0019353 A1 | 1/2004 | Fried et al. | |
| 2004/0030342 A1 | 2/2004 | Trieu et al. | |
| 2004/0044345 A1 | 3/2004 | DeMoss et al. | |
| 2004/0059334 A1 | 3/2004 | Weaver et al. | |
| 2004/0073218 A1 | 4/2004 | Dahners | |
| 2004/0087954 A1 | 5/2004 | Allen et al. | |
| 2004/0097942 A1 | 5/2004 | Allen | |
| 2004/0102773 A1 | 5/2004 | Morrison et al. | |
| 2004/0138666 A1 | 7/2004 | Molz, IV et al. | |
| 2004/0199169 A1 | 10/2004 | Koons et al. | |
| 2004/0210217 A1 | 10/2004 | Baynham et al. | |
| 2004/0210219 A1 | 10/2004 | Bray | |
| 2004/0220566 A1 | 11/2004 | Bray | |
| 2005/0010223 A1 | 1/2005 | Gotfried | |
| 2005/0049593 A1 | 3/2005 | Duong et al. | |
| 2005/0055024 A1 | 3/2005 | James et al. | |
| 2005/0070904 A1 | 3/2005 | Gerlach | |
| 2005/0107796 A1 | 5/2005 | Gerlach et al. | |
| 2005/0273099 A1 | 12/2005 | Baccelli et al. | |
| 2006/0079900 A1 | 4/2006 | Mathieu et al. | |
| 2006/0116678 A1 | 6/2006 | Impellizzeri | |
| 2006/0149247 A1 | 7/2006 | Frigg et al. | |
| 2006/0149265 A1 | 7/2006 | James | |
| 2006/0167464 A1 | 7/2006 | Allen et al. | |
| 2007/0276386 A1 | 11/2007 | Gerlach | |

FOREIGN PATENT DOCUMENTS

| | | |
|---|---|---|
| DE | 196 29 011 A1 | 1/1998 |
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| FR | 2 757 370 | 6/1998 |
| JP | 2002-082896 | 3/2002 |
| WO | WO 97/09000 | 3/1997 |
| WO | WO 99/38447 | 8/1999 |
| WO | WO 00/53110 | 9/2000 |
| WO | WO 00/53111 | 9/2000 |
| WO | WO 01/19264 A2 | 3/2001 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |
| WO | WO 2005/032386 A1 | 4/2005 |
| WO | WO 2006/007965 A1 | 1/2006 |

OTHER PUBLICATIONS

Brochure entitled Introducing the Profile™ Anterior Thoracolumbar Compression Plate, by Dupuy Motech, one page, undated.
Baumgaertel, et al., "Fracture healing in biological plate osteosynthesis," *Injury*, 29(Supp. 3):S-C3-S-C6 (1998).
Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).
Farouk, et al., "Minimally invasive plate osteosynthesis and vascularity: preliminary results of a cadaver injection study," *Injury*, 28(Supp. 1):S-A7-S-A12 (1997).
Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).
Frigg, et al., "The development of the distal femur Less Invasive Stabilization System (LISS)," *Injury, Int. J. Care Injured*, 32(S-C24-31 (2001).
Frigg, et al. "LCP: The Locking Compression Plate System," *Bone Zone* (undated).
Gerber, et al., "Biological internal fixation of fractures," *Arch. Orthop. Trauma Surg.*, 109:295-303 (1990).
Karnezis, et al., "'Biological' internal fixation of long bone fractures: a biomechanical study of a 'noncontact' plate system," *Injury*, 29(9):689-695 (1998).
Koval, et al., "Distal Femoral Fixation : A Biomechanical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).
Krettek, et al., "Intraoperative control of axes, rotation and length in femoral and tibial fractures," *Injury*, 29(Supp. 3):S-C-29-S-C39 (1998).
Marti, et al., "Biomechanical Evaluation of the Less Invasive Stabilization System for the Internal Fixation of Distal Femur Fractures," *Journal of Orthopaedic Trauma*, 15(7):482-487, 2001.
Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).
Mudgal, et al., 'Plate and Screw Design in Fractures of the Hand and Wrist,' *Clinical Orthopaedics and Related Research*, 445:68-80 (2006).
Rüedi, et al., "New Techniques in Indirect Reduction of Long Bone Fractures," *Clinical Orthopaedics and Related Research*, No. 347:27-34 (1998).
Schavan, et al., "LISS—The Less Invasive Stabilization System for Metaphyseal Fractures of Femur and Tibia," *OTA 98 Posters* (1998).
Brochure entitled Quantum Medical Concepts, Tension Booster™ 'A simple device that will help reduce wrist fatigue. It's the little things that can make a difference,' 10 pages, powered by blanco media (undated) http://www.quantummedicalconcepts.com/home.cfm.
*Synthes* (U.S.A.) v. *Smith & Nephew, Inc.*, 03-0084 (E.D. Pa.). Second Supplement to Apr. 9, 2008 Expert Report of J. Lawrence Marsh, M.D. Sep. 3, 2008.
*Synthes* (U.S.A.) v. *Smith & Nephew, Inc.*, 03-0084 (E.D. Pa.). Second Supplement to Apr. 9, 2008 Expert Report of David Seligson, M.D, Sep. 5, 2008.
*Synthes* (U.S.A.) v. *Smith & Nephew, Inc.*, 03-0084 (E.D. Pa.). Smith & Nephew's Memorandum in Support of Its Motion for Partial Summary Judgment of Noninfringement of Claims 1, 6, 14, and 15 of U.S. Patent No. 6,623,486. Sep. 10, 2008.
*Synthes* (U.S.A.) v. *Smith & Nephew, Inc.*, 03-0084 (E.D. Pa.). Smith & Nephew's Memorandum in Support of Its Motion for Partial Summary Judgment of Invalidity of Claims 10-12 of U.S. Patent No. 6,623,486. Sep. 10, 2008.
*Synthes* (U.S.A.) v. *Smith & Nephew, Inc.*, 03-0084 (E.D. Pa.). Declarations of Robert A. King in Support of Smith & Nephew, Inc.'s Motion for Partial Summary Judgment of Invalidity of Claims 10-12 of U.S. Patent No. 6, 623, 486. Sep. 10, 2008.
*Synthes* (U.S.A.) v. *Smith & Nephew, Inc.*, 03-0084 (E.D. Pa..). "Declaration of Kristin J. Doyle in Support of Smith & Nephew's Opposition to Synthes' Motion for Summary Judgment of No Invalidity of the Weaver Patents Over the K982222 Reference.", Sep. 29, 2008.
The Titanium Distal Radius Plate: Technique Guide. Synthes (USA), 1997.
The Titanium Distal Radius Plate: Technique Guide. Synthes (USA), 1994.
Koval et al. "Distal Femoral Fixation: A Biochemical Comparison of the Standard Condylar Buttress Plate, a Locked Buttress Plate, and the 95-Degree Blade Plate". *Journal of Orthopaedic Trauma*. vol. 2.(No. 7) (OVID electronic database version) Oct. 1997: 521-524.
Koval et al. "Distal Femoral Fixation: A Biochemical Comparison of the Standard Condylar Buttress Plate, a Locked Buttress Plate, and the 95-Degree Blade Plate". *Journal of Orthopaedic Trauma*. vol. 2 (No. 7) (in color and as published on Internet) Oct. 1997: 521-524.
Koval et al. "Distal Femoral Fixation: A Biochemical Comparison of the Standard Condylar Buttress Plate, a Locked Buttress Plate, and the 95-Degree Blade Plate". *Journal of Orthopaedic Trauma*. vol. 2 (No. 7) Oct. 1997: 521-524.
*Synthes* (U.S.A.) v. *Smith & Nephew, Inc.*, 03-0084 (E.D. Pa.). Supplement to Apr. 9, 2008 Expert Report of J. Lawrence Marsh, M.D. May 14, 2008.
*Synthes* (U.S.A.) v. *Smith & Nephew, Inc.*, 03-0084 (E.D. Pa.). Second Supplement to Apr. 9, 2008 Expert Report of J. Lawrence Marsh, M.D. Sep. 3, 2008.
*Synthes* (U.S.A.) v. *Smith & Nephew, Inc.*, 03-0084 (E.D. Pa.). Expert Report of John F. Witherspoon. Apr. 9, 2008.
*Synthes* (U.S.A.) v. *Smith & Nephew, Inc.*, 03-0084 (E.D. Pa.). Supplement to Expert Report of John F. Witherspoon. May 14, 2008.

Bolhofner, Brett R. et al. "The Results of Open Reduction and Internal Fixation of Distal Femur Fractures Using a Biologic (Indirect) Reduction Technique." *Journal of Orthopaedic Trauma*. vol. 10. (No. 6) 1996: 372-377.

Kassab, Safa S. et al. "Patients Treated for Nonunions with Plate and Screw Fixation and Adjunctive Locking Nuts." *Clinical Orthopaedics and Related Research*. No. 347. Feb. 1998: 86-92.

Kolodziej, Patricia et al. "Biomechanical Evaluation of the Schuhli Nut." *Clinical Orthopaedics and Related Research*. No. 347. Feb. 1998: 79-85.

Witten, Celia M. Letter to Sheri L. Musgnung (Synthes (USA)) Regarding Section 501(k) Notification of Intent to Market Distal Femur Plate System. Jul. 29, 1998.

Schuhli: Technique Guide—An Adjunct to Plating Problematic Fractures. Synthes (USA) 1998.

Vattolo, Mauro. "The Effect of Grooves in Osteosynthesis Plates on the Restructuring of the Corticalis." Diss. University of Bern, Switzerland, 1986

Less Invasive Stablization System (LISS)—Distal Femur Technique Guide. Synthes (USA), 2000.

Less Invasive Stablization System (LISS) Technique Guide. Synthes (USA), 2000.

Basic Percutaneous Instrumentation and Aiming Arm for 4.5mm LCP Condylar Plates Technique Guide. Guide. Synthes (USA), 2005.

Basic Percutaneous Instrument Set for 4.5mm LCP Condylar Plates (Synthes Large Fragment LCP System). Guide. Synthes (USA), 2005.

Fitzpatrick, Daniel C. et al. "Relative Stability of Conventional and Locked Plating Fixation in Osteoporotic Bone." Article Submission to *Journal of Bone and Joint Surgery*. Apr. 18, 2005.

Rothenberg, Peter. *Paoli Spirit*. (Publication for Synthes Consultants) vol. 14, Issue 2. Jun. 1999.

Krikler, S.J. et al. "Evolution of the Locked Internal Fixator (PC-Fix: Part II)" *Injury: International Journal of the Care of the Injured AO ASIF Scientific Supplement*. vol. 32, Supplement 2. Elsevier Science Ltd., Sep. 2001.

Krikler, S.J. et al. "Less Invasive Stabilization System (LISS) for the Distal Femur." *Injury: International Journal of the Care of the Injured. AO ASIF Scientific Supplement*. vol. 32, Supplement 3, Dec. 2001.

Weaver et al. U.S. Appl. No. 09/660,287: Bone Plating System. Information Disclosure Statement Under 37 C.F.R. § 1.97 and § 1.98. Nov. 13, 2000.

Weaver et al. U.S. Appl. No. 09/660,287: Bone Plating System. Second Information Disclosure Statement Under 37 C.F.R. § 1.97 and § 1.98. Jan. 11, 2001.

Weaver et al. U.S. Appl. No. 09/660,287: Bone Plating System. Third Information Disclosure Statement Under 37 C.F.R. § 1.97 and § 1.98. Feb. 16, 2001.

Brace et al. U.S. Appl. No. 09/453,911: Bone Fixation Assembly. Second Information Disclosure Statement Under 37 C.F.R. § 1.97 and § 1.98. Oct. 2, 2000.

Brace et al. U.S. Appl. No. 09/848,251: Bone Fixation Assembly. Information Disclosure Statement Under 37 C.F.R. § 1.97 and § 1.98. May 4, 2001.

Nemecek, Deborah. Faxed Letter to Jeff Mast, M.D. Regarding Schuhli Surgical Technique Guide Updates to Illustrations. Jun. 15, 1998.

Nemecek, Deborah. Faxed Letter to Jeff Mast, M.D. Regarding Schuhli Surgical Technique Guide Approval Request for Illustration Changes and Narrative for New X-Ray Case. Jun. 23, 1998.

Nemecek, Deborah. Faxed Letter to Jeff Mast, M.D. Regarding Schuhli Surgical Technique Guide Requesting Approval of Additional Warning Required by Fda and Change of Case #3. Aug. 7, 1998.

Perren, Stephan M. et al. "Early Temporary Porosis of Bone Induced by Internal Fixation Implants: A Reaction to Necrosis, Not to Stress Protection?" *Clinical Orthopaedics and Related Research*.No. 232, Jul. 1998: 139-151.

*Synthes* (U.S.A.) v. *Smith & Nephew, Inc.*, 03-0084 (E.D. Pa.). Declaration of J. Lawrence Marsh, M.D. in Support of Smith & Nephew's, Inc.'s Motion for Partial Summary Judgment of Invalidity of Claims 10-12 of U.S. Patent No. 6, 623,486, Sep. 10, 2008.

*Synthes* (U.S.A.) v. *Smith & Nephew, Inc.*, 03-0084 (E.D. Pa.). Initial Expert Report of J. Lawrence Marsh, M.D. Regarding the Invalidity of the Patents-in-Suit. Apr. 9, 2008.

*Synthes* (U.S.A.) v. *Smith & Nephew, Inc.*, 03-0084 (E.D. Pa.). Smith & Nephew's Memorandum in Support of Its Opposition to Synthes' Motion for Summary Judgment of No Invalidity of the Weaver Patents over the K982222 Reference. Sep. 29, 2008.

*Synthes* (U.S.A.) v. *Smith & Nephew, Inc.*, 03-0084 (E.D. Pa.). Declaration of David Seligson, M.D. in Support of Smith & Nephew's [sic], Inc.'s Motion for Partial Summary Judgment of Invalidity of Claims 10-12 of U.S. Patent No. 6,623,486. Sep. 10, 2008.

*Synthes* (U.S.A.) v. *Smith & Nephew, Inc.*, 03-0084 (E.D. Pa.). (Sealed) Smith & Nephew's Statement of Undisputed Facts in Support of Its Opposition to Synthes' Motion for Summary Judgment of No Invalidity of the Weaver Patents over the K982222 Reference. Sep. 29, 2008.

*Synthes* (U.S.A.) v. *Smith & Nephew, Inc.*, 03-0084 (E.D. Pa.). Smith & Nephew, Inc.'s Opening Brief in Support of Its Claim Constructions. Mar. 16, 2007.

*Synthes* (U.S.A.) v. *Smith & Nephew, Inc.*, 03-0084 (E.D. Pa.). Smith & Nephew, Inc.'s Responsive Brief in Support of Its Claim Construction. Apr. 20, 2007.

*Synthes* (U.S.A.) v. *Smith & Nephew, Inc.*, 03-0084 (E.D. Pa.). Memorandum and Order. Feb. 4, 2008.

Haas, N.P., et. al., "LISS—Less Invasive Stabilization System—A New Internal Fixator for Distal Femur Fractures," OP J., vol. 13(3), pp. 340-344, Georg Thieme Verlag, Dec. 1997 (original in German, translation to English attached with certification).

Order Granting/Denying Request for Ex Parte Reexamination for U.S. Appl. No. 90/009,377 dated Feb. 13, 2009.

Order Granting/Denying Request for Ex Parte Reexamination for U.S. Appl. No. 90/009,378 dated Feb. 14, 2009.

Non-final Office Action in U.S. Appl. No. 11/644,303 mailed Oct. 14, 2009, 19 pages.

USPTO Final Office Action in U.S. Appl. No. 11/644,303 mailed May 14, 2010, 8 pages.

\* cited by examiner

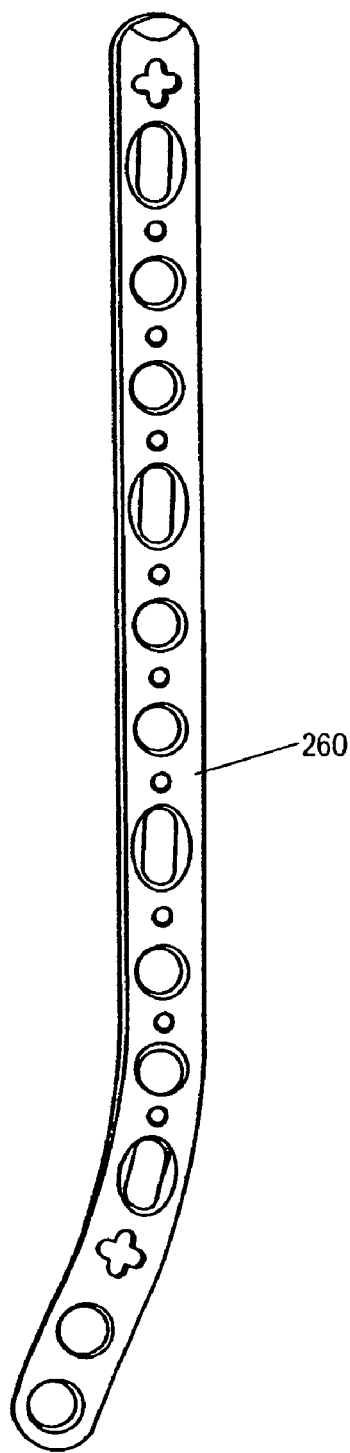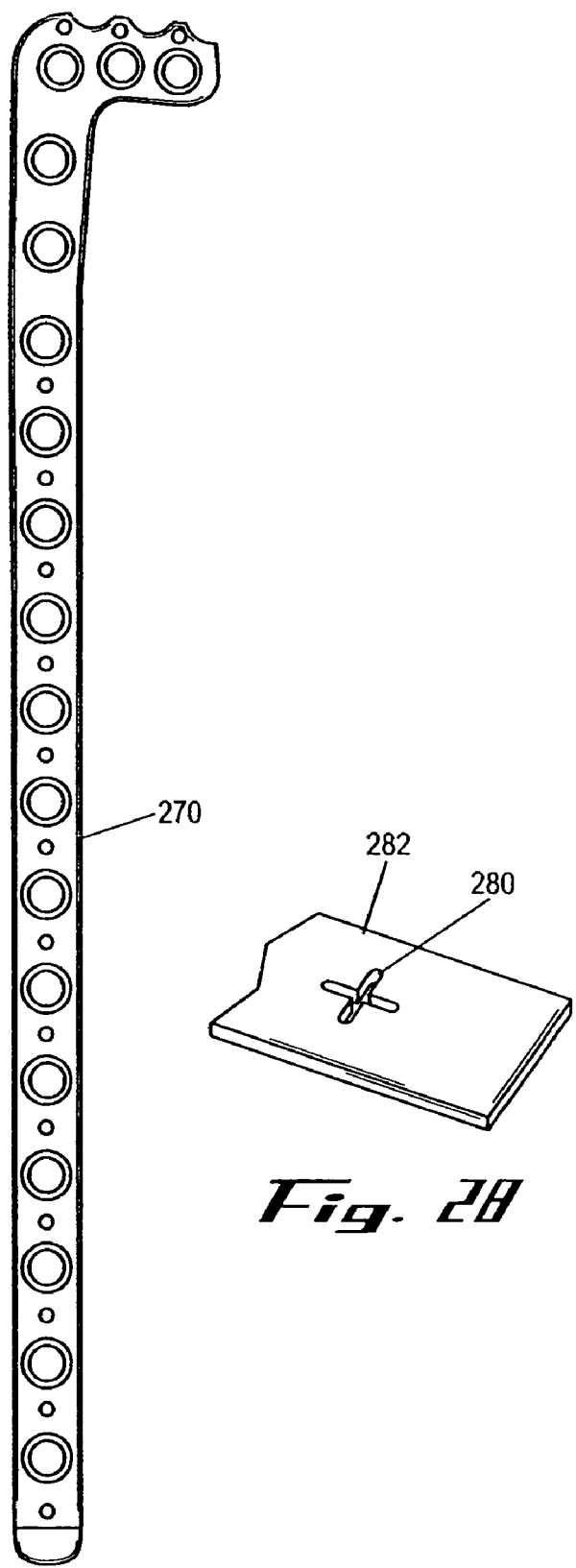
Fig. 26  Fig. 27  Fig. 28

BONE PLATES AND BONE PLATE ASSEMBLIES

This application is a continuation application of U.S. application Ser. No. 10/673,833, filed Sep. 29, 2003, now U.S. Pat. No. 7,179,260 now pending, the entire contents of which are hereby incorporated by reference.

FIELD OF THE INVENTION

The invention relates generally to apparatuses for fixation of parts of a fractured bone, and, more particularly, to bone plates and bone plate assemblies, including bone plates and screws, for stabilization and compression of parts of a fractured bone.

BACKGROUND OF THE INVENTION

Bone fractures lead to complex tissue injuries involving both the bone and the surrounding soft tissue. Treated in a conservative way, fractures often result in malalignment or non-unions and may also lead to stiffness of adjacent joints. To reduce the occurrence of these problems, open reduction and internal fixation of the bone can be carried out. Anatomical reduction and stable internal fixation with plates and screws are very successful in treating bone fractures.

Good bone healing can also result from relative stability, where the clinical outcome is often dependent on obtaining correct length, axis, and rotation of the fractured bone rather than on precise anatomical reduction and absolute stability. To achieve this, while at the same time minimizing the amount of additional soft tissue trauma, treatment of multi-fragmented metaphyseal and diaphyseal fractures with plates and screws was developed.

An existing solution is plate and screw systems where the screws are locked in the plate. The plate and screws form one stable system and the stability of the fracture is dependent upon the stiffness of the construct. No compression of the plate onto the bone is required, which reduces the risk of primary loss of reduction and preserves bone blood supply. Locking the screw into the plate to ensure angular, as well as axial, stability eliminates the possibility for the screw to toggle, slide, or be dislodged and thereby strongly reduces the risk of postoperative loss of reduction. As the relationship between the locking screws and the plate is fixed, locking screws provide a high resistance to shear or torsional forces, but locking screws have a limited capability to compress bone fragments.

Because of this shortcoming, many surgeons began expressing the desire to have plate and screw systems (or bone plate assemblies) where the surgeon can choose intraoperatively whether to use the bone plate with compression screws (also referred to as cortical or cancellous screws), locking screws, or with a combination of both. This led to the development of a combination slot, a compression slot combined with a partially threaded opening, that could receive either a compression screw or a locking screw.

Bone plate assemblies that combine compression screws and locking screws are ideal in certain clinical situations. Bone plates with combination slots, including partially threaded openings, are well known to those skilled in the art. The partially threaded portions allow either locking or compression screws to be used. Because the slots are only partially threaded, the locking screws may not be able to maintain the fixed angular relationship between the screws and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intraoperative plate orientation. Additionally, because of the slot geometry, translation of the plate with compressions screws may be limited to a single direction, which may be disadvantageous in reduction and manipulation of fragments.

Accordingly, there is a need for improved bone plates that may be used with both compression and locking screws for improved stabilization and compression of parts of a fractured bone.

SUMMARY OF THE INVENTION

The present invention provides bone plates and bone plate assemblies for stabilization and compression of parts of a fractured bone. According to an exemplary embodiment of the present invention, a bone plate includes an upper surface, a bone contacting surface, and at least one hole extending through the upper surface and the bone contacting surface that may interchangeably receive a locking screw and a compression screw, wherein each hole includes a thread that makes a complete revolution around the hole.

According to certain exemplary embodiments, each hole may include a top portion extending from the upper surface and a threaded bottom portion extending from the top portion to the bone contacting surface. The top portion of the hole may extend from the upper surface of the bone plate at a first angle relative to the plane of the upper surface. The top portion of the hole may include a ramp extending from the upper surface at a first angle relative to the plane of the upper surface and a concave recessed portion that is generally spherical. The first angle may be fifty-two degrees in either instance. The bottom portion of the hole may be generally cylindrical or tapered with an included angle of less than about thirty degrees. The included angle may be about twenty degrees. Each hole is configured to engage a head of a compression screw and provide compression of fractured bone fragments. Using a compression screw, fine adjustment of a fracture of up to two millimeters in more than one direction is possible. Each hole is configured to threadably engage a head of a locking screw and fix the locking screw with respect to the bone plate.

In another exemplary embodiment, a bone plate includes an upper surface, a bone contacting surface, and at least one hole extending through the upper surface and the bone contacting surface that may interchangeably receive a locking screw and a compression screw, wherein each hole includes (a) a top portion extending from the upper surface and (b) a bottom portion extending from the top portion to the bone contacting surface, wherein the bottom portion is threaded to receive threads of a head of a locking screw and the bottom portion includes at least one thread that makes a complete revolution around the hole. In certain embodiments, the top portion extends from the upper surface at a first angle relative to the plane of the upper surface and the bottom portion is tapered with an included angle of less than about thirty degrees. The first angle may be about fifty-two degrees and the included angle may be about twenty degrees. In certain embodiments, the top portion includes a ramp extending from the upper surface at a first angle relative to the plane of the upper surface and a concave recessed portion that is generally spherical and the bottom portion is generally cylindrical.

In another exemplary embodiment according to this invention, a bone plate assembly includes a bone plate, at least one locking screw, and at least one compression screw. The bone plate includes an upper surface, a bone contacting surface, and at least one hole extending through the upper surface and the bone contacting surface that may interchangeably receive a locking screw and a compression screw, wherein each hole includes a thread that makes a complete revolution around the hole.

In certain exemplary embodiments of a bone plate assembly, a hole is configured to engage a head of the compression screw and provide compression of fractured bone fragments. Each hole may be configured to engage a head of the compression screw such that fine adjustment of a fracture of up to two millimeters in more than one direction is possible and to threadably engage a head of a locking screw and fix the locking screw with respect to the bone plate.

In certain exemplary embodiments of a bone plate assembly, a head of the locking screw may include threads that engage threads in the hole. Both the head of the locking screw and the hole may be tapered. The head of the locking screw and at least a portion of the hole may be tapered at an included angle of less than about thirty degrees. The locking screw may include a head with triple lead threads and a single lead threaded shaft such that all threads of the locking screw are of a constant pitch. In certain embodiments, the lead of threads of the locking screw is not continuous between the threads of the head and the threads of the shaft of the locking screw. Each hole of the bone plate may include a top portion extending from the upper surface and a threaded bottom portion extending from the top portion to the bone contacting surface.

Certain exemplary embodiments of this invention also include methods of reducing a fracture.

BRIEF DESCRIPTION OF THE DRAWINGS

FIGS. 10-27 are perspective views of various exemplary bone plate configurations according to various embodiments of the present invention, without threads of any holes or other openings shown.

FIG. 28 shows a provisional fixation slot according to one embodiment of the present invention.

DETAILED DESCRIPTION OF THE INVENTION

The present invention provides bone plates and bone plate assemblies for stabilization and compression of parts of a fractured bone. According to certain exemplary embodiments of this invention, a bone plate includes an upper surface, a bone contacting surface, and at least one hole extending through the upper surface and the bone contacting surface that may interchangeably receive a locking screw and a compression screw. The bone plate may include additional openings that receive only compression screws or only locking screws.

A threaded head of an exemplary locking screw for use in accordance with this invention is received by threads in a corresponding hole such that the threads of the hole completely surround the threads of the head of the locking screw. This relationship between the head of the locking screw and the threads of the hole contributes to maintaining fixation of the bone plate and strengthening the plate and screw combination. As noted, a compression screw may also be received within the hole of the bone plate. As the compression screw is fully inserted within a bone, the head of the compression screw comes into contact with and rides along a top portion of the hole, allowing for fine adjustment of the position of the bone plate in more than one direction.

Figure 1A:
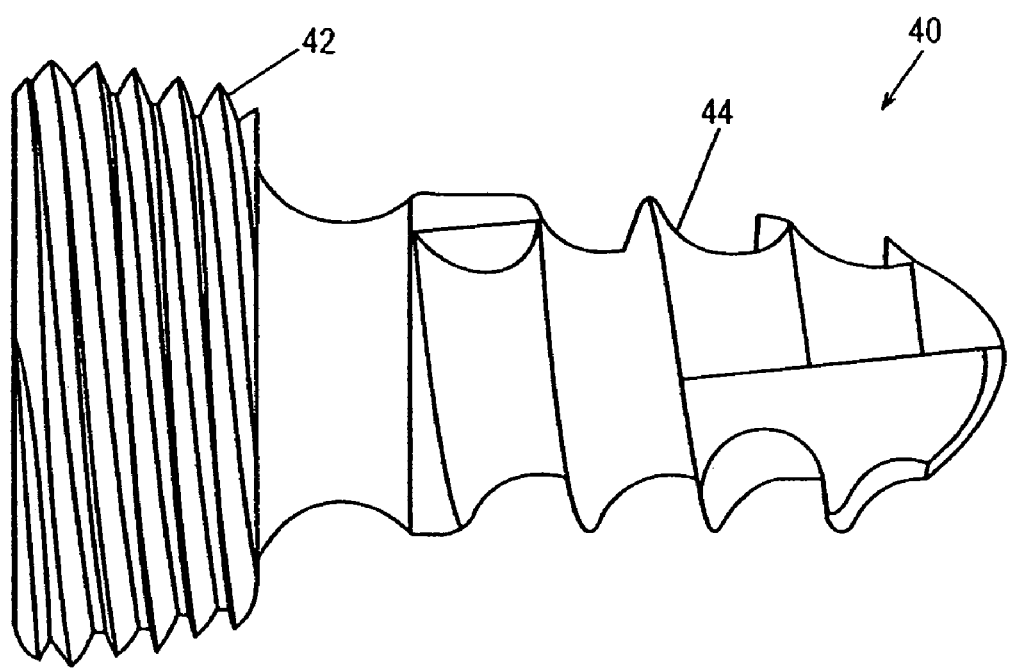
FIG. 1A shows a side view of an exemplary locking screw according to one embodiment of the present invention.
Figure 1B:
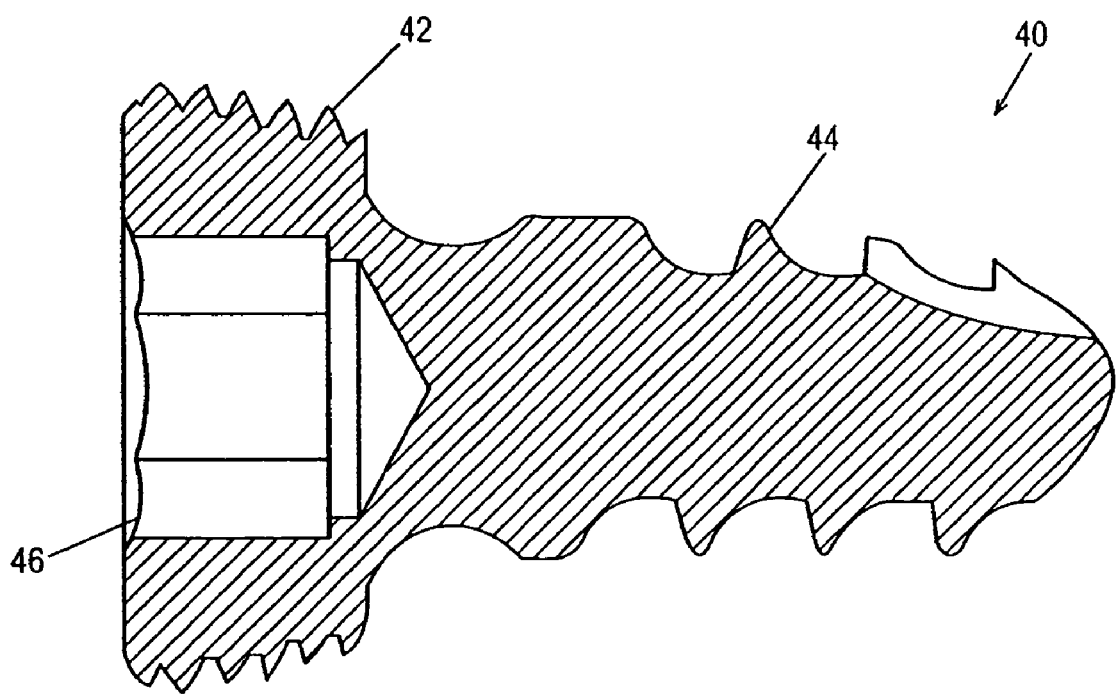
FIG. 1B shows a cross-sectional view of the locking screw of FIG. 1A.

FIGS. 1A and 1B show an exemplary locking screw for use according to one embodiment of the present invention. A locking screw 40 includes a threaded head 42 and a threaded shaft 44. Locking screw 40 may be a 3.5 mm, 4.5 mm, 6.5 mm, or other size locking screw, which is understood by those skilled in the art. In the exemplary embodiment shown in FIGS. 1A and 1B, the lead between the threads of head 42 and the threads of shaft 44 is broken. The threads in shaft 44 of locking screw 40 are single lead and the threads in head 42 are triple lead, providing locking screw 40 with same pitch throughout. It is preferable for certain embodiments of locking screws according to this invention to have a constant pitch. In an exemplary 3.5 mm locking screw, the pitch is 1.25 mm and the angle of the thread form is about 45 to about 60 degrees. In an exemplary 4.5 mm locking screw, the pitch is 1.75 mm and the angle of the thread form is about 60 degrees. Locking screw 40 also includes an internal hex head 46, as shown in FIG. 1B, that is used when tightening locking screw 40 into a bone plate and/or bone.

FIGS. 2A-2E show different views of a portion of a bone plate according to an embodiment of the present invention. Such bone plates generally include one or more holes or other openings, such as in the exemplary bone plates shown in FIGS. 10-27, which are briefly described below. However, for ease of illustration and for purposes of describing an exemplary embodiment of the present invention, only a portion of bone plate 50 is shown in FIGS. 2A-2E.

Figure 2A:
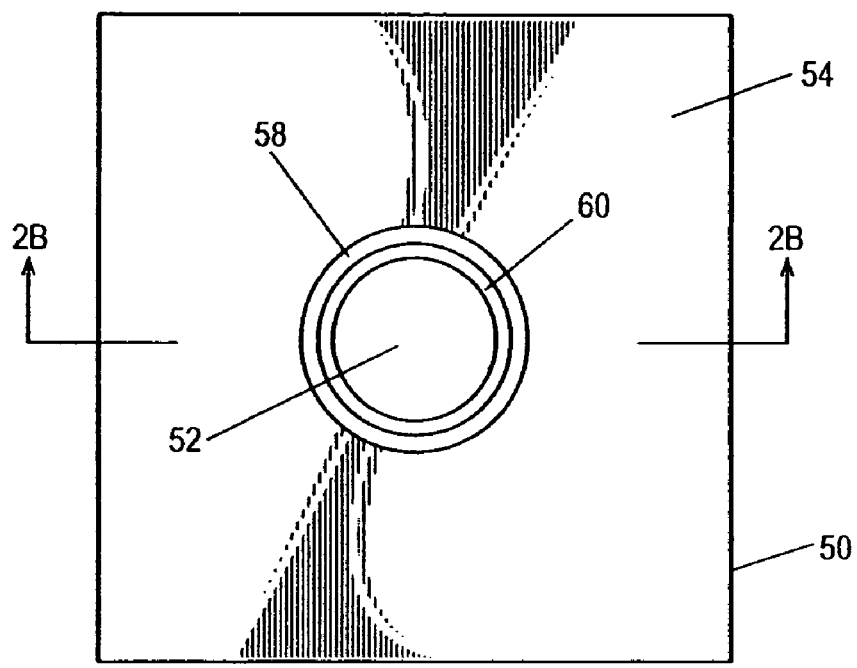
FIG. 2A shows a top view of a portion of a bone plate, including a hole without the threads of the hole shown, according to one embodiment of the present invention.
Figure 2B:
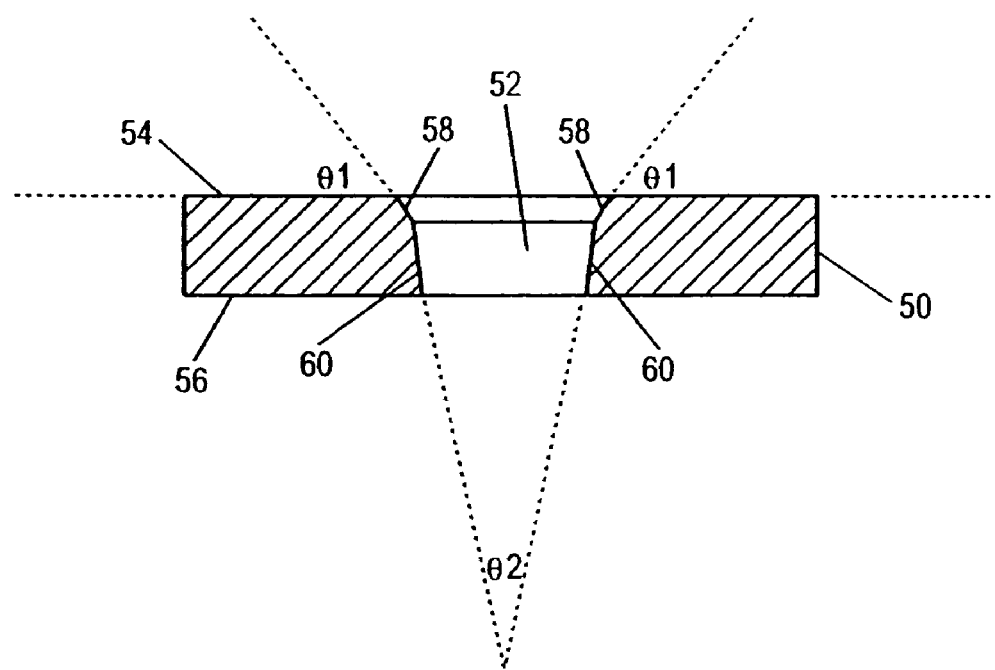
FIG. 2B shows a cross-sectional view of the portion of the bone plate shown in FIG. 2A as viewed along cross-section lines 2B-2B of FIG. 2A.
Figure 2C:
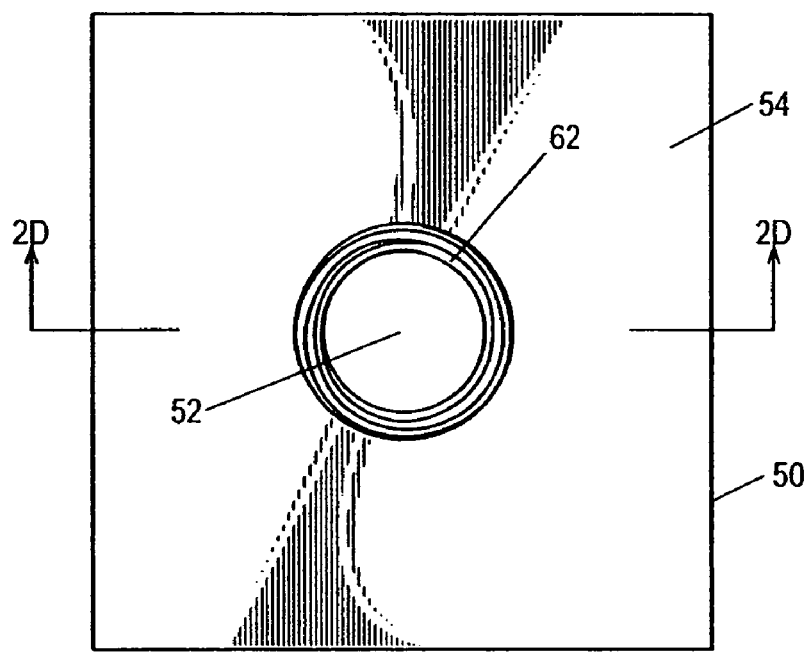
FIG. 2C shows a top view of the portion of the bone plate shown in FIGS. 2A and 2B, with the threads of the hole shown.
Figure 2D:
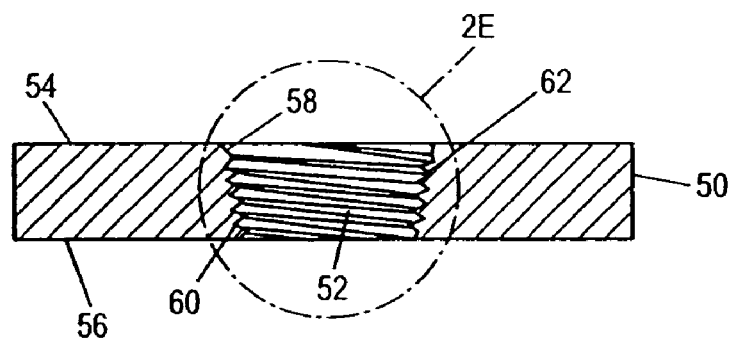
FIG. 2D shows a cross-sectional view of the portion of the bone plate shown in FIGS. 2A-2C as viewed along cross-section lines 2D-2D of FIG. 2C.
Figure 2E:
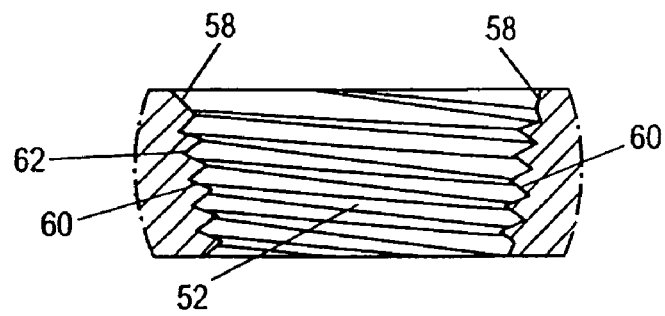
FIG. 2E shows a detailed view of the hole of the portion of the bone plate shown in FIGS. 2A-2D.

The particular bone plate 50 shown in these drawings includes a hole 52 extending through an upper surface 54 and a bone contacting surface 56 of bone plate 50. FIGS. 2A and 2B show hole 52 without its threads to help illustrate certain aspects of this embodiment of the invention, while FIGS. 2C-2E show hole 52 with its threads. It should be understood that the geometry of hole 52 is the same throughout these drawings, although the geometry of hole 52 is not as clearly visible in the drawings that show the threads of hole 52. As seen most clearly in FIG. 2B, hole 52 includes a top portion 58 extending downward from upper surface 54. Top portion 58 is generally frustoconical in shape and extends from upper surface 54 at an angle of θ1 relative to the plane of top surface 54, as shown in FIG. 2B. In an exemplary embodiment, angle θ1 is about fifty-two degrees.

A bottom portion 60 of hole 52 extends from the end of top portion 58 through bone contacting surface 56 of bone plate 50. Bottom portion 60 includes threads 62, as shown in FIGS. 2C-2E. Some of threads 62 may extend into top portion 58 depending on the particular embodiment, but top portion 58 is not completely threaded.

In the exemplary embodiment shown in FIGS. 2A-2E, bottom portion 60 is tapered. The included angle, θ2 shown in FIG. 2B, of the taper of bottom portion 60 may be less than about thirty degrees, including zero degrees (i.e., no taper at all). The larger the included angle, the larger hole 52 in bone plate 50 must be, which begins to compromise the strength of the plate if the included angle is much larger than about thirty degrees. In an exemplary embodiment, θ2 is about twenty degrees.

Figure 3:
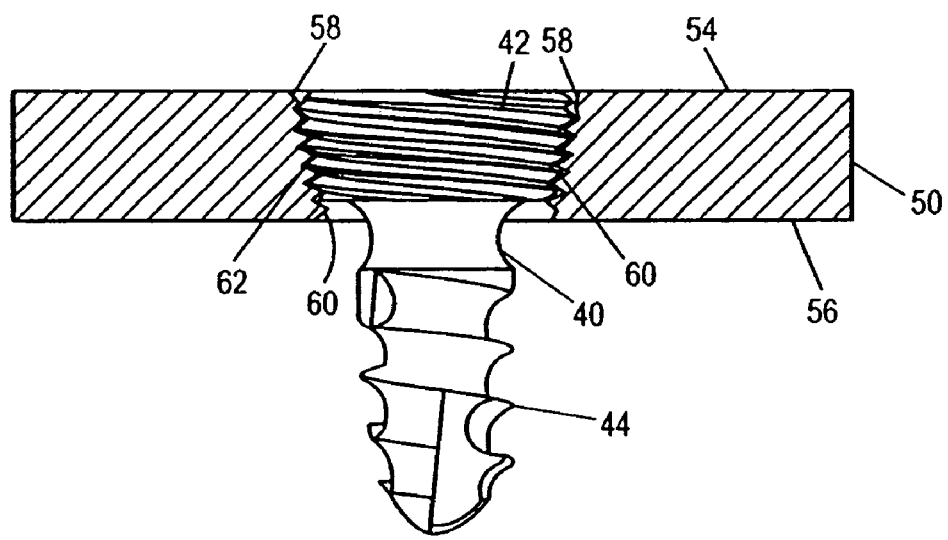
FIG. 3 shows a side view of the locking screw of FIGS. 1A and 1B threaded into the portion of the bone plate shown in FIGS. 2A-2E.

FIG. 3 shows a side view of locking screw 40 threaded into hole 52 of bone plate 50. Head 42 of locking screw 40 is received by threads 62 of bone plate 50. Threads 62 completely surround the threads of head 42, and the top of head 42 is received completely within hole 52 such that head 42 of locking screw 40 sits flush with upper surface 54 of bone plate 50. Shaft 44 of locking screw 40 is threaded into bone (not shown). Head 42 of locking screw 40 should be tapered such that it properly mates with threads 62 of hole 52 of bone plate 50. Furthermore, a threaded portion of a head of a locking screw for use with certain embodiments of this invention should have a taper generally corresponding to the taper, if any, of the threads of the hole of the bone plate.

Figure 4:
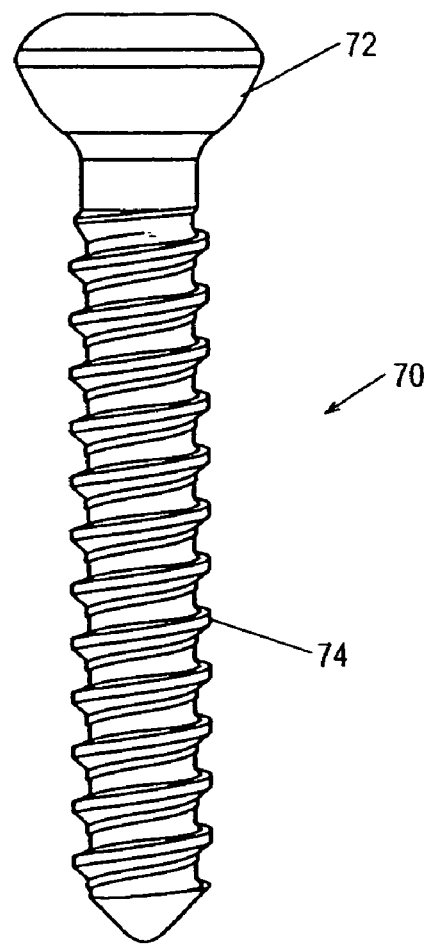
FIG. 4 shows a side view of an exemplary compression screw for use according to one embodiment of the present invention.
Figure 5:
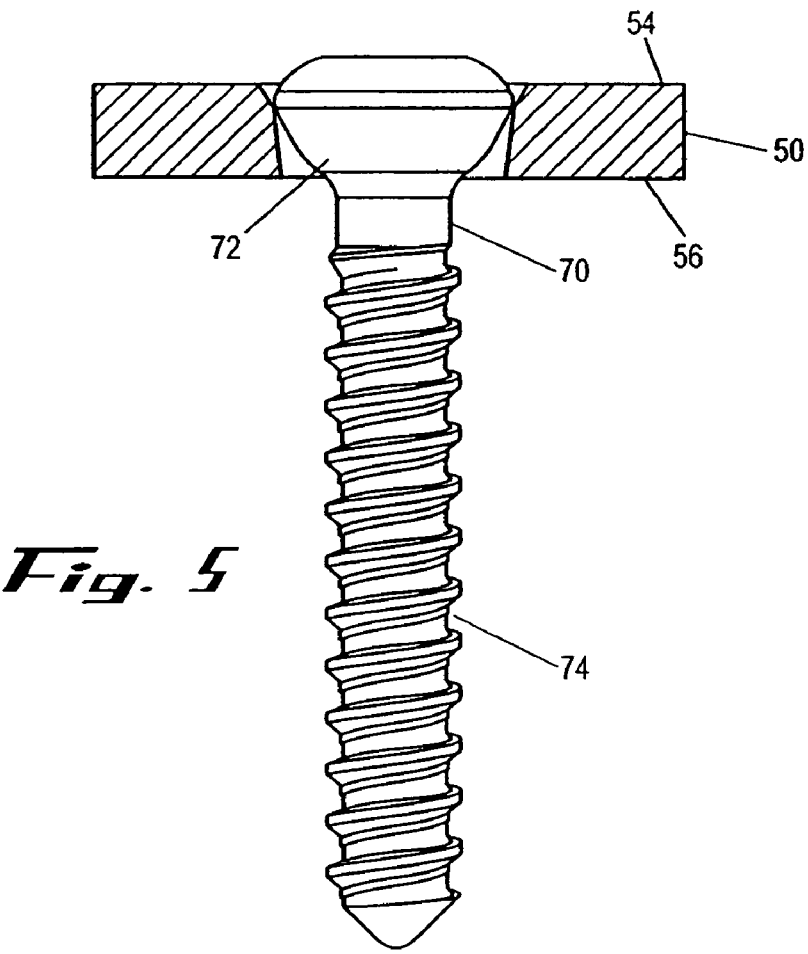
FIG. 5 shows a side view of the compression screw of FIG. 4 inserted into the portion of the bone plate shown in FIGS. 2A-2E.

FIG. 4 shows a side view of an exemplary compression screw for use according to an embodiment of the present invention. A compression screw 70 includes a head 72 and a threaded shaft 74 for engaging a bone. Head 72 is preferably spherical, as shown in the drawings. FIG. 5 shows compression screw 70 inserted within hole 52 of bone plate 50. As shown in FIG. 5, head 72 of compression screw 70 rides along top portion 58 of bone plate 50. As shown clearly in FIG. 5, the diameter of shaft 74 is less than the diameter of the opening at bottom portion 60 of hole 52. Thus, as shaft 74 is threaded into a bone (not shown), compression screw 70 may pull or push bone plate 50 in a particular direction as the spherical head 72 of compression screw 70 comes into contact with and rides along the frustoconical top portion 58 of hole 52 of bone plate 50. The angle θ1, shown in FIG. 2B, at top portion 58 of hole 52 is significant for compression of a fracture and is necessary to help shift the bone plate in the desired direction. If top portion 58 were to extend straight down from upper surface 54 of bone plate 50, compression would be less successful. Compression screw 70 may move bone plate 50 in more than one direction as compression screw 70 is fully inserted within hole 52. In an exemplary embodiment, fine adjustment of fractures up to about two millimeters in several directions is possible.

Figure 6A:
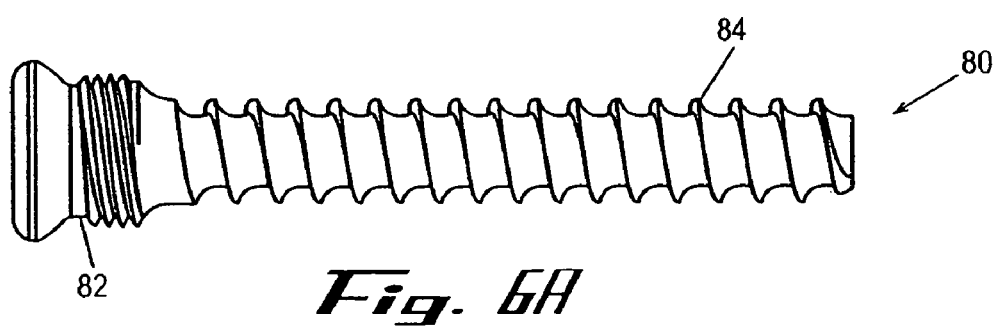
FIG. 6A shows a side view of an exemplary locking screw according to an embodiment of the present invention.
Figure 6B:
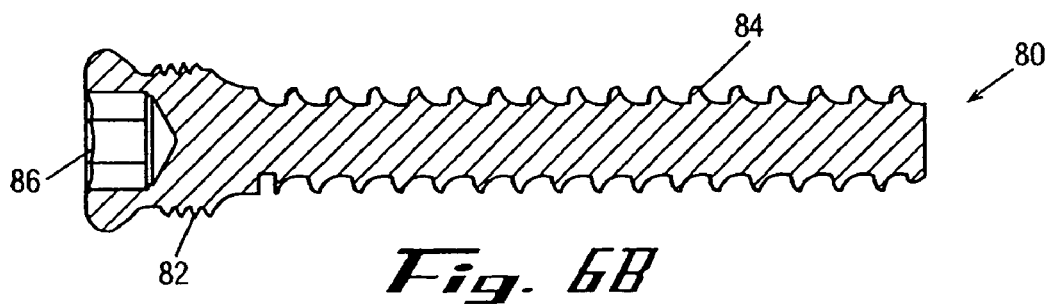
FIG. 6B shows a cross-sectional view of the locking screw of FIG. 6A.

FIGS. 6A and 6B show another exemplary locking screw for use according to an embodiment of the present invention. A locking screw 80 includes a head 82 and a threaded shaft 84. Similar to locking screw 40 shown in FIGS. 1A and 1B, locking screw 80 may be a 3.5 mm, 4.5 mm, 6.5 mm, or other size locking screw, which is understood by those skilled in the art, and the lead between the threads of head 82 and the threads of shaft 84 is broken. The threads in shaft 84 of locking screw 80 are single lead and the threads in head 82 are triple lead, providing locking screw 80 with the same pitch throughout. The pitches and angles of thread form for exemplary 3.5 and 4.5 mm locking screws 80 are generally similar to those described above with reference to locking screw 40.

Locking screw 80 also includes an internal hex head 86, as shown in FIG. 6B, that is used when tightening locking screw 80 into a bone plate and/or bone. As may be seen from FIGS. 1A, 1B, 6A, and 6B, only a portion of head 82 of locking screw 80 is threaded, whereas the entire head 42 of locking screw 40 is threaded. Additionally, the threaded portion of head 82 of locking screw 80 is not tapered, while head 42 of locking screw 40 is tapered. These differences are because locking screw 40 is designed to mate with hole 52 of bone plate 50, while locking screw 80 is designed to mate with a hole 92 of a bone plate 90, as further described below.

Figure 7A:
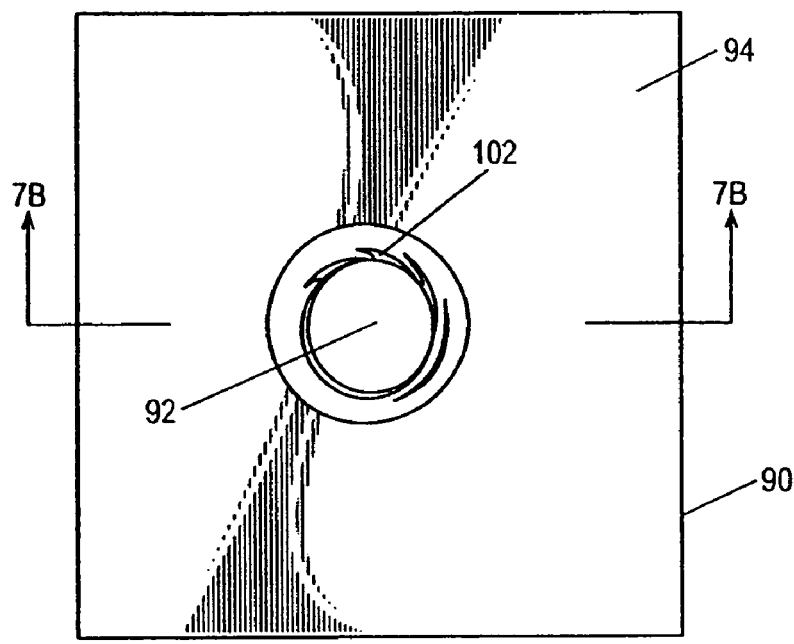
FIG. 7A shows a top view of a portion of a bone plate according to an embodiment of the present invention.
Figure 7B:
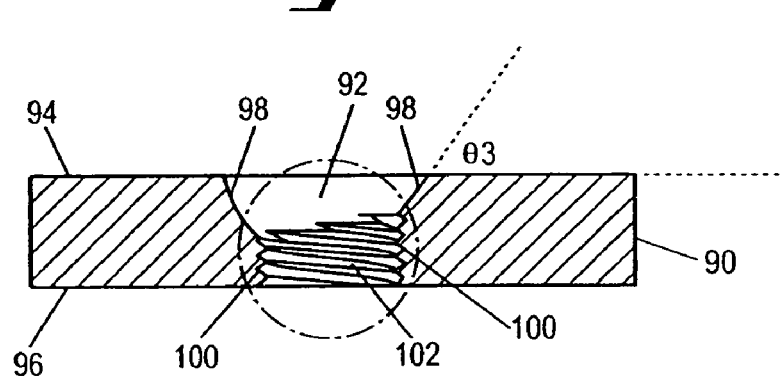
FIG. 7B shows a cross-sectional view of the portion of the bone plate shown in FIG. 7A as viewed along cross-section lines 7B-7B of FIG. 7A.
Figure 7C:
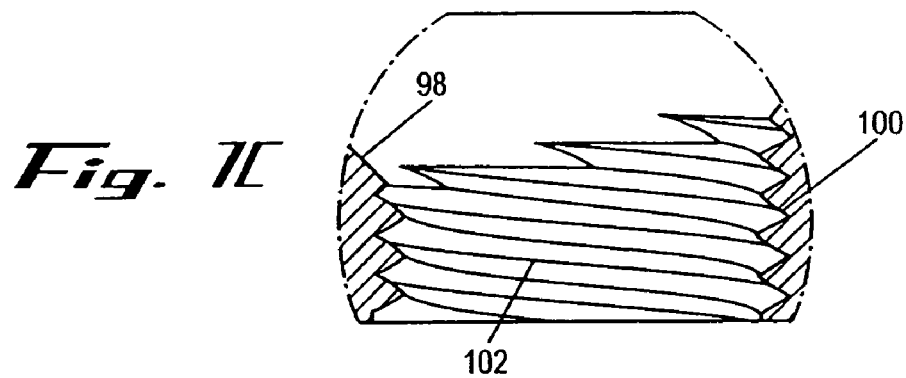
FIG. 7C shows a detailed view of the hole of the portion of the bone plate shown in FIGS. 7A and 7B.

FIGS. 7A-7C show different views of a portion of a bone plate according to an embodiment of the present invention. As noted above, bone plates generally include one or more holes or other openings, such as in the exemplary bone plates shown in FIGS. 10-27, but for ease of illustration, only a portion of bone plate 90 is shown in FIGS. 7A-7C.

Bone plate 90 includes a hole 92 extending through an upper surface 94 and a bone contacting surface 96 of bone plate 90. Hole 92 includes a top portion 98 extending downward from upper surface 94. As shown in FIG. 7B, one side of top portion 98 includes a ramp that extends from upper surface 94 at an angle of θ3 relative to the plane of top surface 94. In an exemplary embodiment, angle θ3 is about fifty-two degrees. The remainder of top portion 98 is a concave recessed portion that is generally spherical in shape, as shown in FIG. 7B. Although of a slightly different structure than top portion 58 of hole 52, top portion 98 of hole 92 also has a generally frustoconical shape, as shown in the figures.

A bottom portion 100 of hole 92 extends from the end of top portion 98 through bone contacting surface 96 of bone plate 90. Bottom portion 100 includes threads 102. Some of threads 102 may extend into top portion 98 depending on the particular embodiment, but top portion 98 generally has only the beginning of thread leads, if any threading. Bottom portion 100 is not tapered, but rather is generally cylindrical in shape. In certain embodiments, for example, bottom portion 60 of hole 52 of bone plate 50, bottom portion 100 may be tapered at an included angle of less than about thirty degrees.

Figure 8:
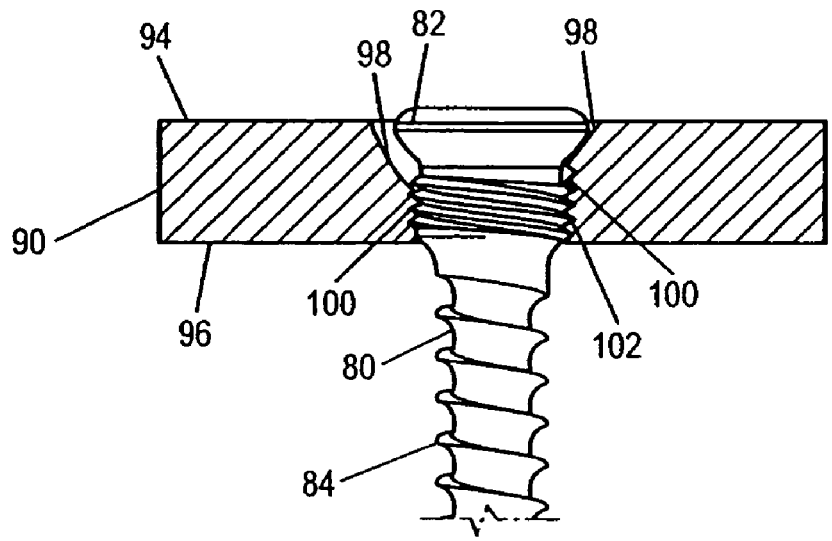
FIG. 8 shows a side view of the locking screw of FIGS. 6A and 6B threaded into the portion of the bone plate shown in FIGS. 7A-7C.

FIG. 8 shows a side view of locking screw 80 threaded into hole 92 of bone plate 90. Threads of head 92 of locking screw 90 are received by threads 102 of bone plate 90. Threads 102 completely surround the threads of head 92, and shaft 84 of locking screw 80 is threaded into bone (not shown). Head 82 of locking screw 80 is shaped such that its unthreaded portion bears against the ramp of top portion 98 of hole 92 of bone plate 90. Additionally, the threaded portion of head 82 is generally cylindrical (i.e., not tapered) so that it properly mates with threads 102 of hole 92 of bone plate 90. A threaded portion of a head of a locking screw for use with certain embodiments of this invention should be shaped to generally correspond to the shape of threaded portion of the hole of the bone plate.

Figure 9:
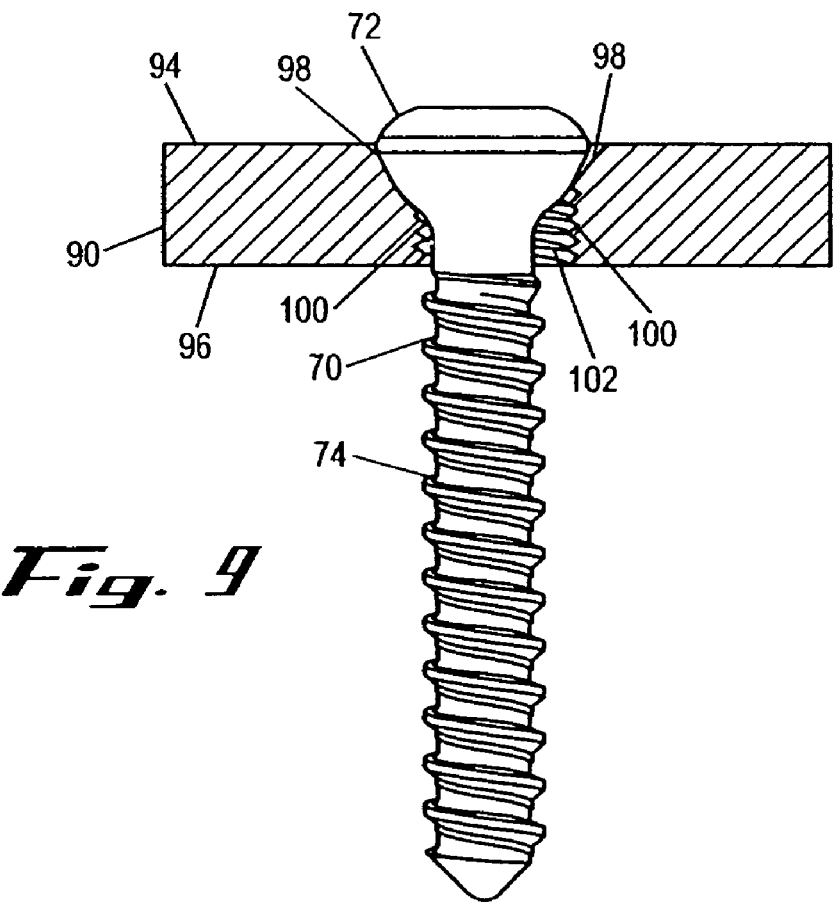
FIG. 9 shows a side view of the compression screw of FIG. 4 inserted into the portion of the bone plate shown in FIGS. 7A-7C.

FIG. 9 shows compression screw 70 inserted within hole 92 of bone plate 50. As shown in FIG. 9, head 72 of compression screw 70 sits within the frustoconical top portion 98, contacting the concave recessed area of top portion 98 of bone plate 90. Head 72 of compression screw 70 contacts the ramp area of top portion 98, but head 72 does not completely abut the ramp. As shown clearly in FIG. 9, the diameter of shaft 74 is less than the diameter of the opening at bottom portion 100 of hole 92. Thus, as shaft 74 is threaded into a bone (not shown), compression screw 70 may pull or push bone plate 90 in a particular direction as spherical head 72 of compression screw 70 comes into contact with and rides along the frustoconical top portion 98 of hole 92 of bone plate 90, similar to that described above with reference to FIG. 5. The angle θ3, shown in FIG. 7B, at top portion 98 of hole 92 is significant for compression of a fracture and is necessary to help shift the bone plate in the desired direction. If top portion 98 were to extend straight down from upper surface 94 of bone plate 90, compression would be less successful. Compression screw 70 may move bone plate 90 in more than one direction as compression screw 70 is fully inserted within hole 92. In an exemplary embodiment, fine adjustment of fractures up to about two millimeters in several directions is possible.

In practice, a first screw is initially inserted through a bone plate and into a bone on one side of a fracture and then a second screw is inserted through the bone plate on the opposite side of the fracture. In an exemplary method according to an embodiment of the present invention, after the first screw is in place, a compression screw is inserted through a hole in the bone plate on a side of the fracture opposite the side of the first screw. The compression screw may be inserted through the hole and into the bone such that as the compression screw is fully inserted, the bone plate is drawn over to a desired position. By moving the bone plate, the tissue is being pulled together to reduce the fracture. Once the compression screw has been used to move the bone plate into the desired position, the compression screw may be removed from the bone and bone plate and a locking screw may be inserted through the hole in the bone plate and in the bone in the space formerly occupied by the compression screw. The locking screw can then be tightened to lock the plate into position. The replacement of the compression screw with the locking screw is not required, but a locking screw may provide more stability and rigid fixation than leaving the compression screw in place. In some modes of operation, a locking screw is placed directly in a locking hole without first inserting a compression screw in the hole. Certain embodiments of the invention contemplate using locking screws and compression screws in any order and in combination or not in combination with each other. As described above, certain embodiments of this invention provide for fine adjustment of fractures in more than one direction.

FIGS. 10-27 show various exemplary bone plate configurations that may include one or more holes, such as holes 52 and 92 described above, that are capable of interchangeably receiving compression screws and locking screws. Exemplary bone plates may also include other openings configured to receive only locking screws or only compression screws, which is well understood by those skilled in the art. All holes in the exemplary plates of FIGS. 10-27 include threads (not shown), while the other generally non-circular openings in these plates may or may not include threads depending on the purposes for which the opening is to be used.

Figure 10:
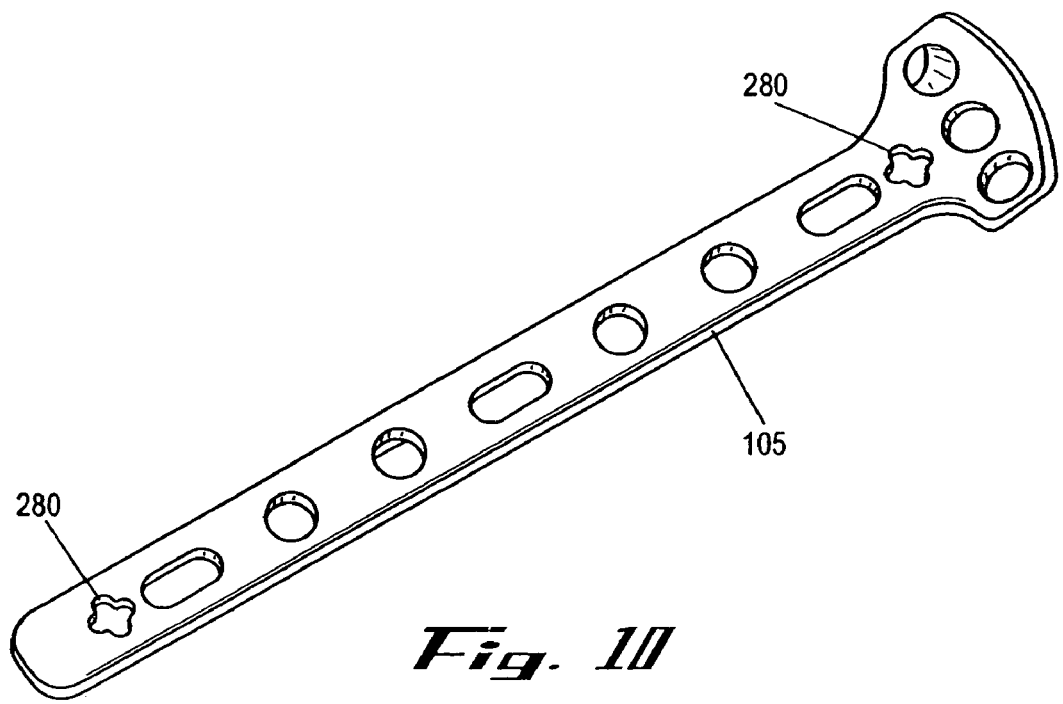
Figure 11:
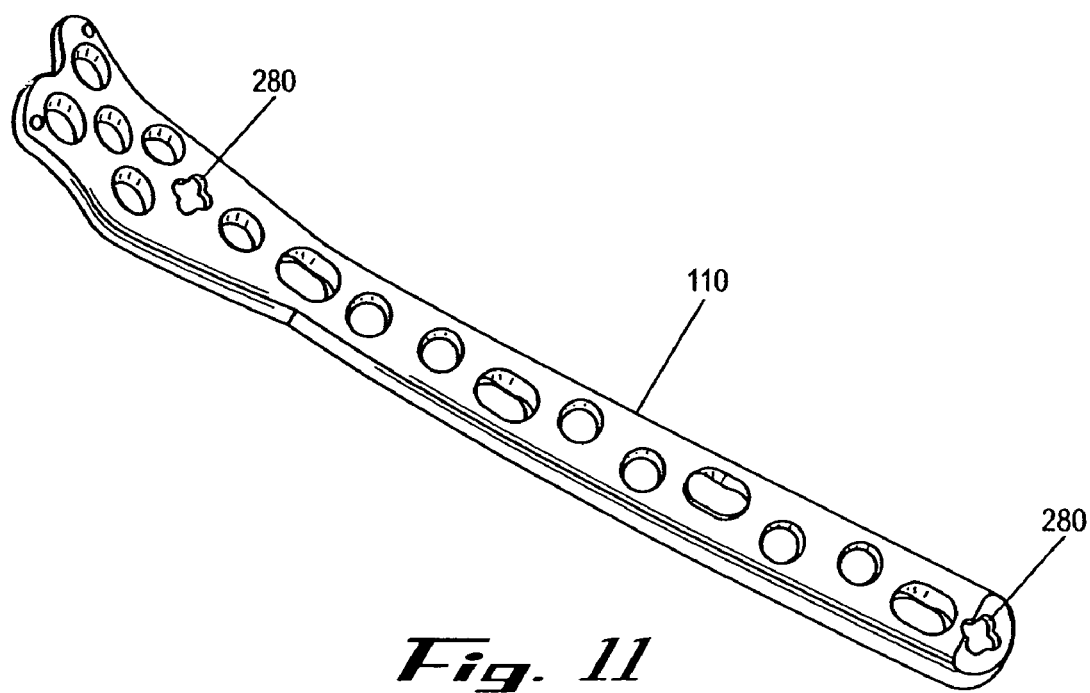
Figure 12:
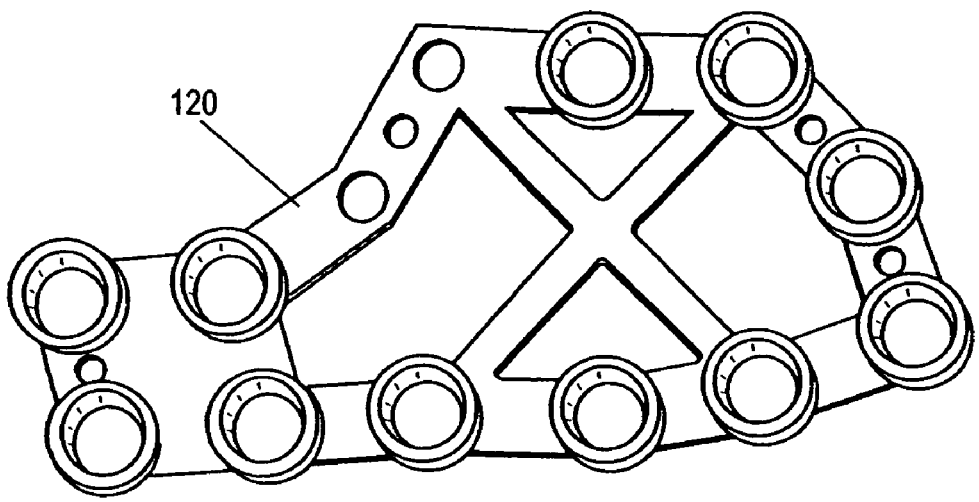
Figure 13:
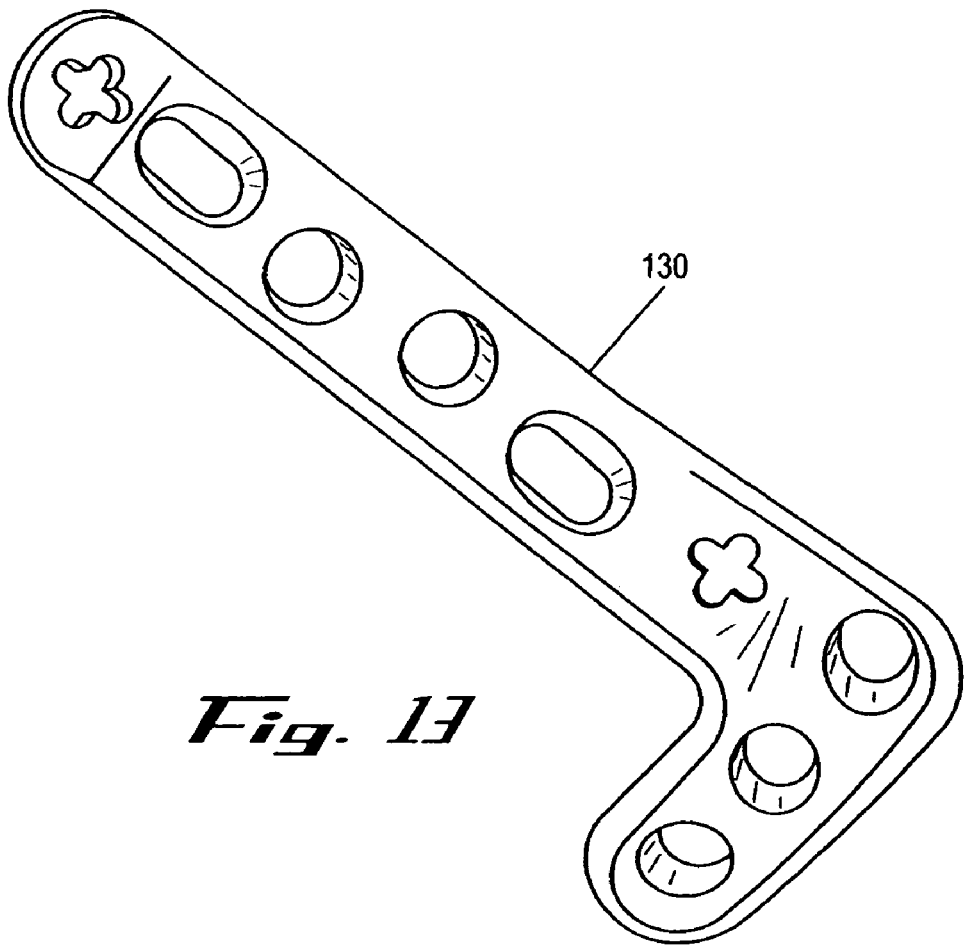
Figure 14:
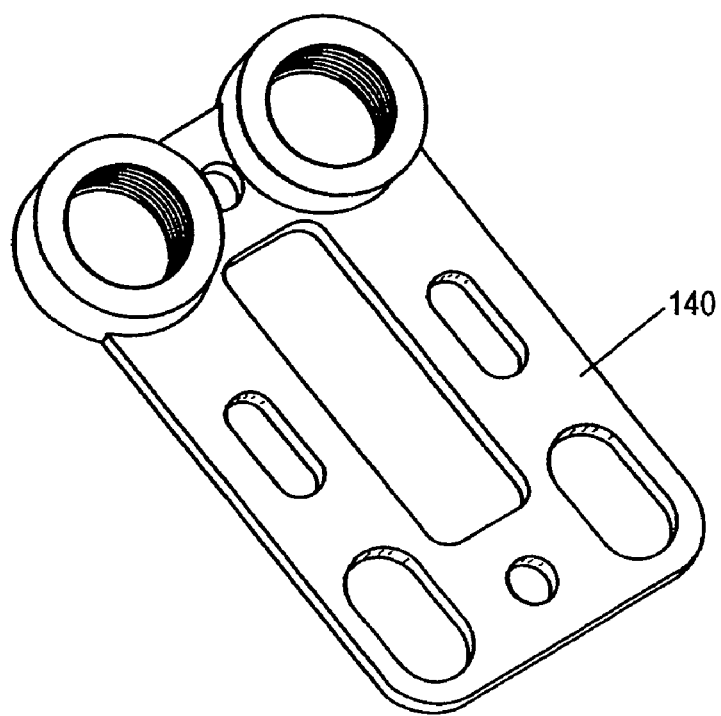
Figure 15:
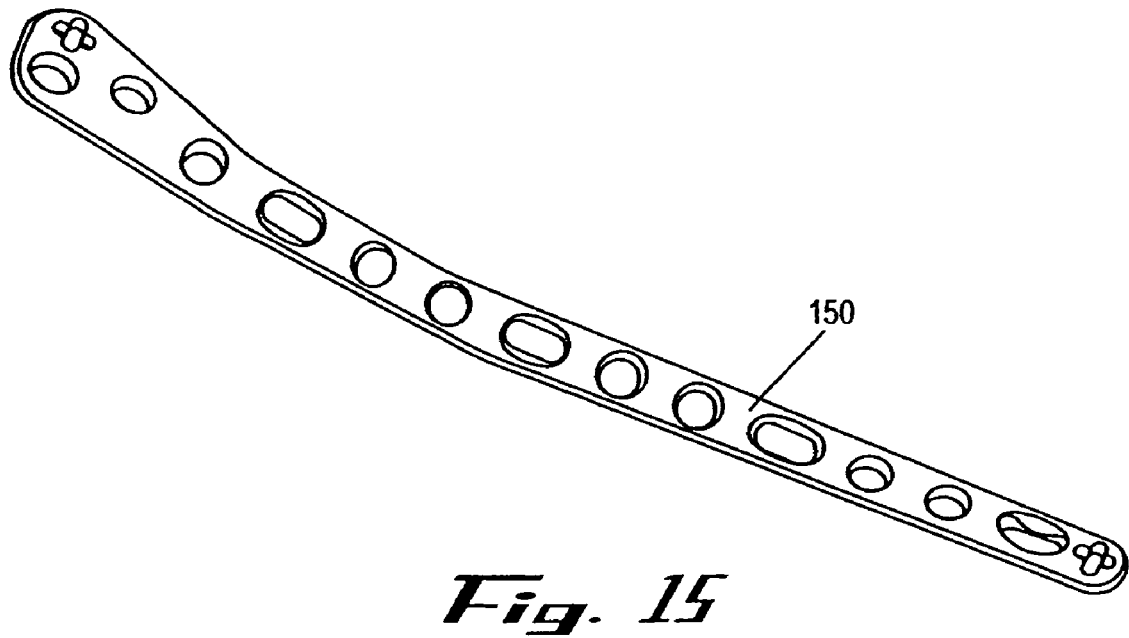
Figure 16:
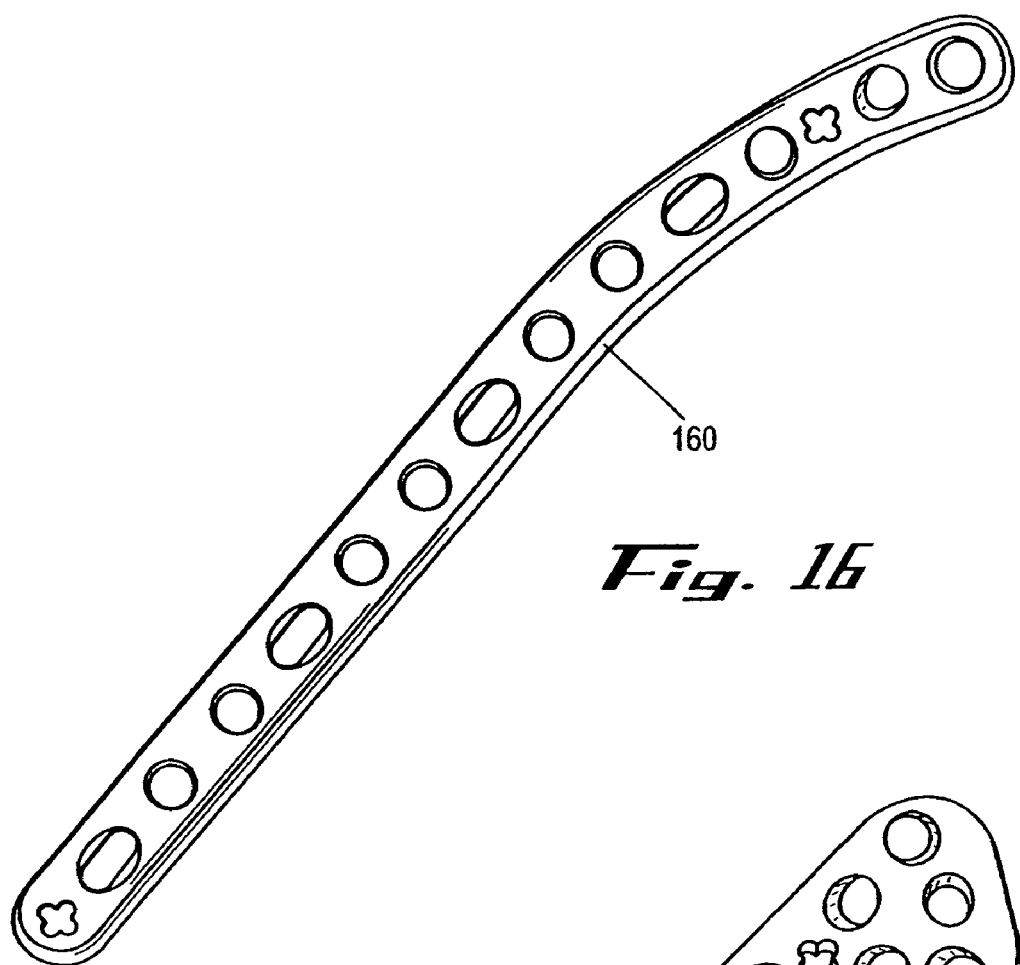
Figure 17:
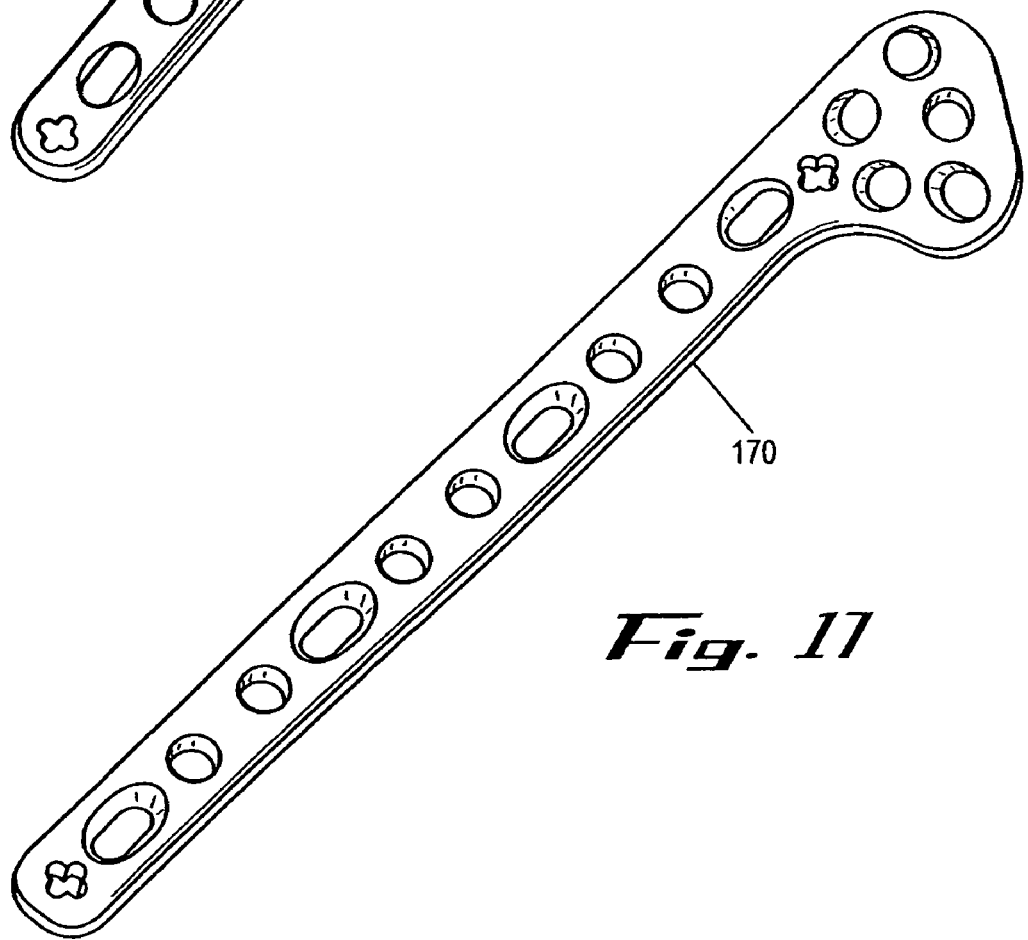
Figure 18:
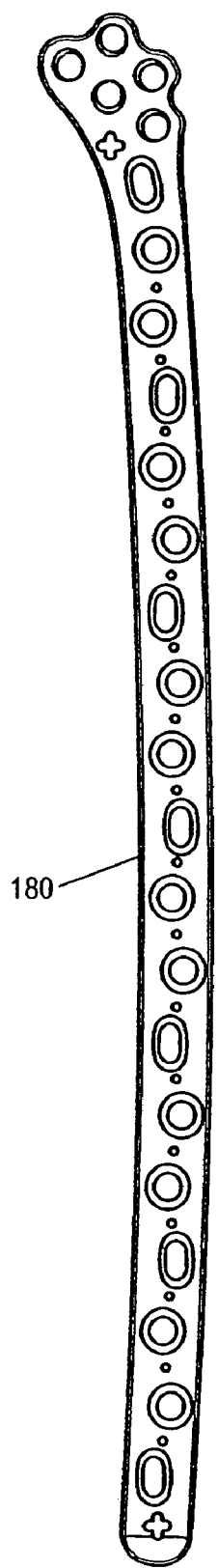

FIG. 10 shows a distal radius plate 105 that is applied on the volar aspect of the radius and used to treat fractures of the distal radius. FIG. 11 shows a distal tibia plate 110 used to treat distal tibia fractures and contoured to match the anatomy of the medial distal tibia. FIG. 12 shows a calcaneal plate 120 that is applied to the medial aspect of the calcaneus and used to treat calcaneal fractures. FIG. 13 shows a distal tibia plate 130 used to threat distal tibia fractures and contoured to match the anatomy of the lateral anterior distal tibia. FIG. 14 shows a multipurpose plate 140 used in conjunction with the calcaneal plate to fuse the talus to the calcaneus. FIG. 15 depicts a distal fibula plate 150 used to treat distal fibula fractures from the lateral side of the bone. FIG. 16 illustrates a bone plate 160 used to treat the medial distal humerus. FIG. 17 shows a proximal humerus plate 170 contoured to match the anatomy of the lateral proximal humerus. FIG. 18 illustrates a distal femur plate 180 contoured to treat fractures of the distal femur from the lateral side of the bone.

Figure 19:
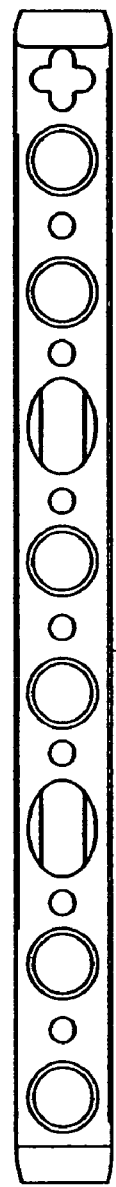
Figure 20:
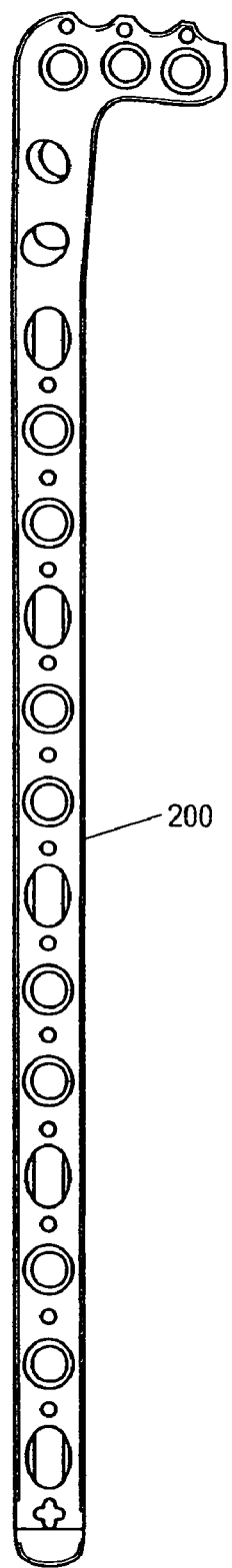
Figures 21, 22, 23:
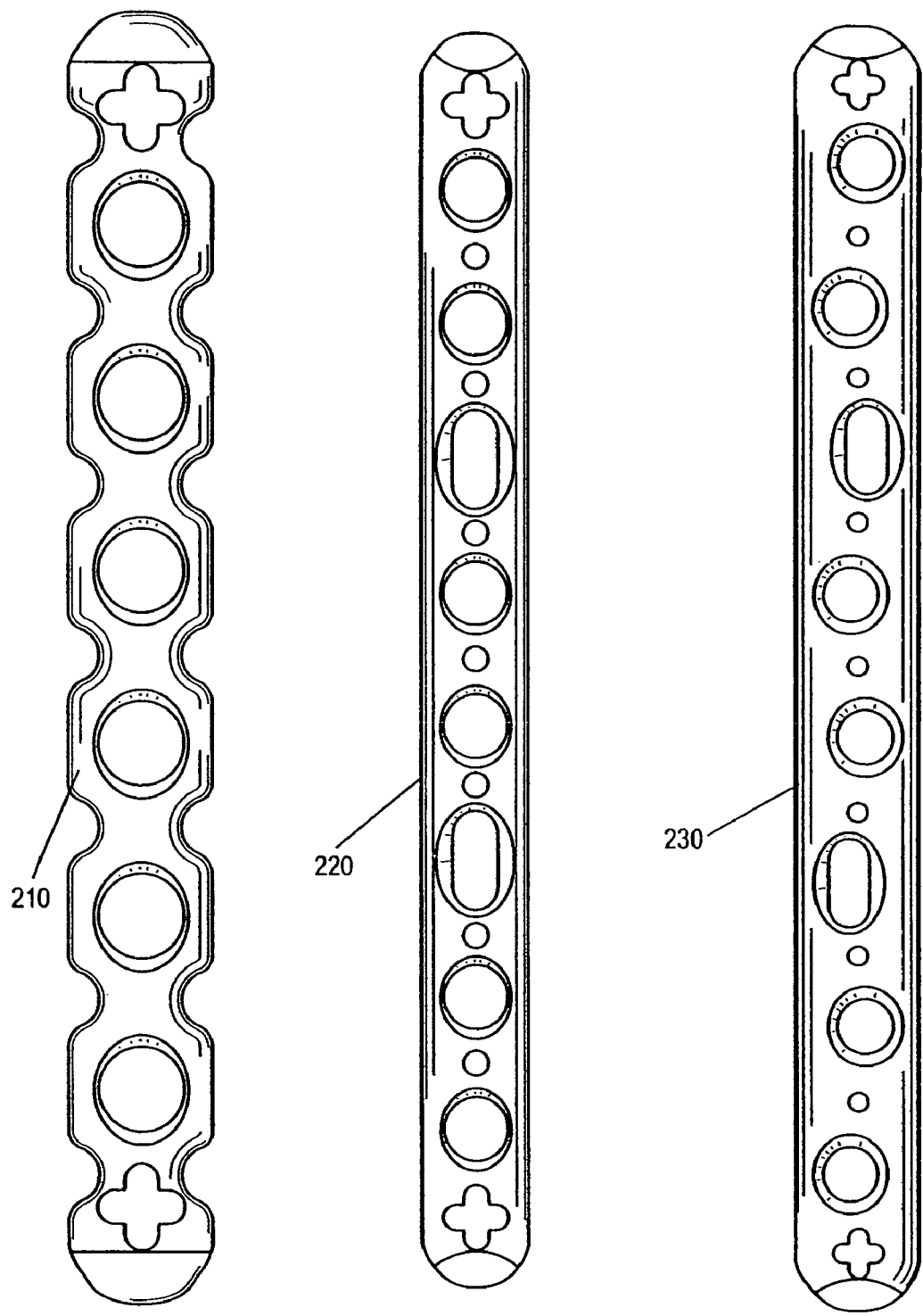
Figure 24:
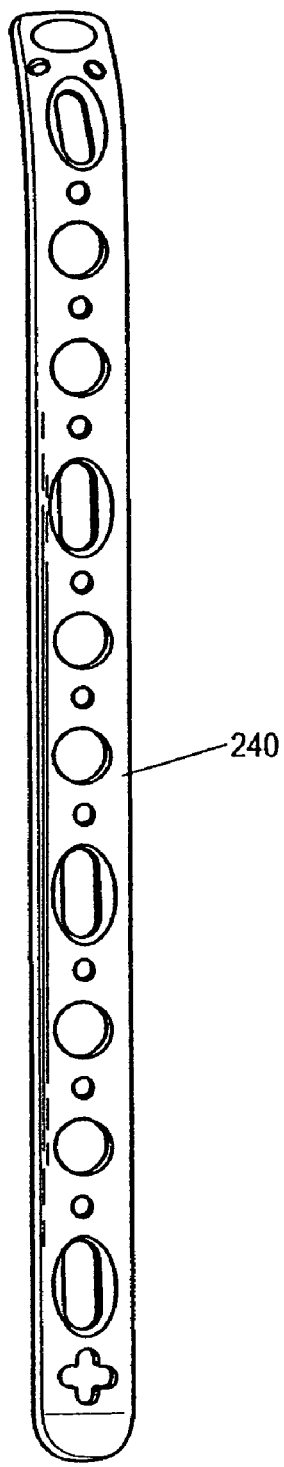
Figure 25:
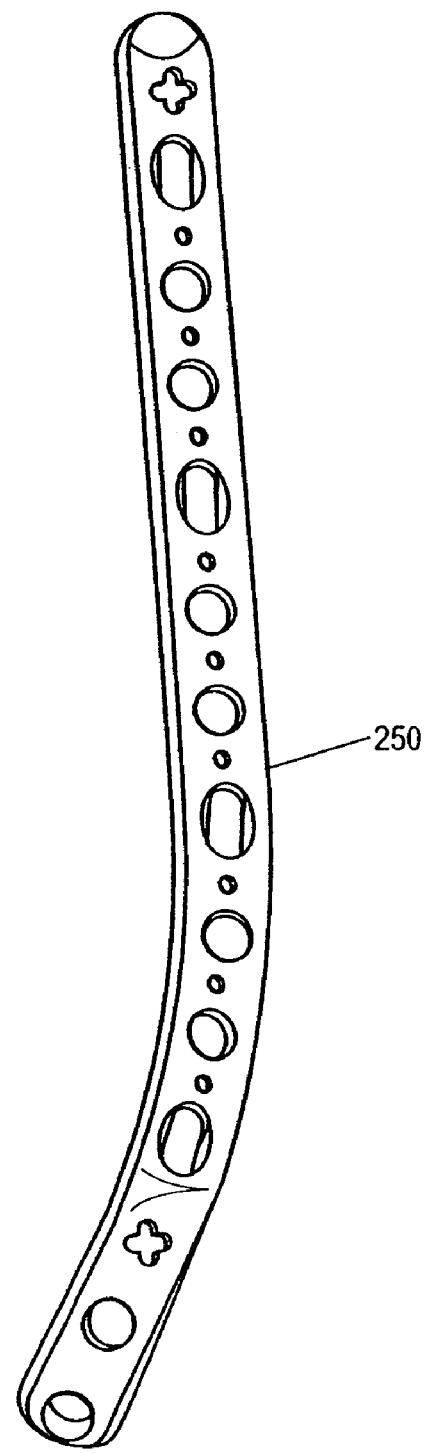

FIG. 19 shows a ⅓ tubular straight bone plate 190 used to treat small bone fractures. FIG. 20 depicts a proximal tibia plate 200 contoured to treat proximal tibia fractures from the medial side. FIG. 21 shows a reconstruction plate 210. FIG. 22 illustrates a small fragment straight plate 220, and FIG. 23 illustrates a large fragment bone plate 230. FIG. 24 illustrates an olecranon plate 240 used to treat fractures of the proximal ulna. FIG. 25 shows a distal humerus plate 250 contoured to match the anatomy of the lateral posterior distal humerus. FIG. 26 depicts a distal humerus plate 260 contoured to match the anatomy of the lateral distal humerus. FIG. 27 shows a proximal tibia plate 270 contoured to treat proximal tibia fractures from the medial side that is similar to plate 200, except that plate 270 includes only holes, such as hole 52 and hole 92, that may receive both compression and locking screws and does not include any other openings.

Shown in some of the exemplary bone plates in FIGS. 10-27 are provisional fixation slots, such as, for example, slots 280 in FIGS. 10 and 11, according to one embodiment of the present invention. FIG. 28 shows provisional fixation slot 280 in a portion of a bone plate 282. As is well known to those skilled in the art, provisional fixation pins are commonly used to provisionally affix a bone plate to the bone prior to installation of the bone plate with permanent attachment, such as bone screws. Existing provisional fixation slots typically allow only fixation of bone fragments and not any adjustability of the position of bone fragments. An embodiment of a provisional fixation slot of this invention allows articulation of bone fragments in up to six degrees of freedom to reduce the bone fracture. A bone fragment may be locked into a position and then incrementally repositioned to another temporary or permanent location. In FIG. 28, slot 280 has a cross or x shape, but the shape of slot 280 may vary according to the desired functionality and may include I, L, T, and other shape slots.

In practice, a bone plate is placed on the bone and the plate may or may not be affixed to the bone utilizing bone screws and/or provisional fixation pins. When provisional fixation is desired, a provisional fixation pin may be inserted through a provisional fixation slot and driven into the target bone fragment. The fragment may be manipulated to reduce the fracture and draw the fragment to the plate. Once the bone fragment is in a desired position, the provisional fixation pin may be tightened until the pin locks into the plate. If further movement of the bone fragment is desired, a second provisional fixation pin may be inserted in the same provisional fixation slot in a space in the slot that is not occupied by the first pin. After insertion of the second pin, the first pin may be removed and the bone fragment may be manipulated with the second pin. Once a desired position of the bone fragment is reached, the second pin is locked into the bone plate. Standard devices well known to those skilled in the art, such as screws, pins, cables, and other devices, may be used to affix the bone to the bone plate. Once the construct is sufficiently stable, any provisional fixation pins in use may be removed from the bone.

The foregoing description of exemplary embodiments of the invention has been presented only for the purposes of illustration and description and is not intended to be exhaustive or to limit the invention to the precise forms disclosed. Many modifications and variations are possible in light of the above disclosure. The embodiments were chosen and described in order to explain the principles of the invention and their practical application so as to enable others skilled in the art to make and utilize the invention and various embodiments and with various modifications as are suited to the particular use contemplated. Alternative embodiments will become apparent to those skilled in the art to which the present invention pertains without departing from its spirit and scope.

What is claimed is:

1. A method for reducing a fracture of a bone, comprising:
   inserting a first fastener through a hole in a bone plate and into engagement with bone, the hole extending between a first surface and a second surface of the bone plate and having a smooth, tapered portion extending from the first surface of the bone plate and a threaded tapered portion extending from the second surface of the bone plate;
   contacting a non-threaded head of the first fastener with the smooth, tapered portion of the hole to move the bone plate in a desired direction relative to the bone;
   removing the first fastener from the hole; and
   inserting a second fastener through the hole and into engagement with the bone such that a threaded head of the second fastener engages the threaded tapered portion of the hole.

2. The method of claim 1, wherein inserting the first fastener comprises inserting a compression screw through the hole and inserting the second fastener comprises inserting a locking screw through the hole.

3. The method of claim 1, further comprising inserting one or more provisional fixation pins through the bone plate and into engagement with the bone.

4. The method of claim 3, further comprising adjusting the one or more provisional fixation pins to draw a bone fragment to the bone plate.

5. The method of claim 1, wherein the bone plate is adjusted up to about two millimeters in the desired direction.

6. A method for reducing a bone fracture, comprising:
   placing a bone plate against the bone, the bone plate defining a through hole extending between a first surface and a second surface of the bone plate and having a smooth, tapered first portion extending from the first surface of the bone plate and a preformed, threaded tapered second portion extending from the second surface of the bone plate, the first and second portions being tapered at different angles, wherein the through hole is configured to receive a first fastener and a second fastener; and
   inserting one of the first fastener and the second fastener through the through hole and into engagement with the bone such that a non-threaded head of the first fastener contacts the smooth, tapered first portion of the through hole to move the bone plate in a desired direction relative to the bone to provide axial compression of the fracture of the bone or such that a threaded head of the second fastener engages the threaded tapered second portion of the through hole to maintain fixation of the bone plate relative to the bone.

7. The method of claim 6, wherein the first fastener is a compression screw and the second fastener is a locking screw.

8. The method of claim 6, further comprising inserting one or more provisional fixation pins through the bone plate and into engagement with the bone.

9. The method of claim 8, wherein the bone plate further comprises a provisional fixation slot in the bone plate.

10. The method of claim 9, wherein the one or more provisional fixation pins are configured for insertion through the provisional fixation slot and into engagement with the bone.

11. A method for reducing a bone fracture, comprising:
    placing a bone plate against bone, the bone plate comprising an upper surface and a lower surface and defining a through hole extending between the upper surface and the lower surface, the through hole comprising a first region extending from the upper surface and a second region extending from the lower surface, the first region being smooth and configured to engage a non-threaded head of a compression screw and the second region having performed threads that make a complete revolution around the second region and that are configured to engage a threaded head of a locking screw; and
    inserting one of a compression screw and a locking screw through the through hole and into engagement with bone such that the non-threaded head of the compression screw contacts the first region to move the bone plate in a desired direction relative to the bone to provide axial compression of the bone fracture or such that the threaded head of the locking screw engages the second region of the through hole to maintain fixation of the bone plate relative to the bone.

12. The method of claim 11, further comprising adjusting the position of the bone and surrounding tissue by adjusting the insertion of the compression screw by up to about two millimeters in more than one direction.

13. The method of claim 11, further comprising inserting the compression screw through the through hole such that the non-threaded head of the compression screw contacts the first region and rides along the first region allowing for adjustment of up to about two millimeters in a desired direction.

14. A method for reducing a bone fracture, comprising:
    placing a bone plate against bone, the bone plate comprising an upper surface and a lower surface and defining a first through hole and a second through hole, each of the first and second through holes extending between the upper surface and the lower surface, the first through hole comprising a first region extending from the upper surface and a second region extending from the lower surface, the first region being smooth and configured to engage a non-threaded head of a compression screw and the second region having performed threads that make a complete revolution around the second region and that are configured to engage a threaded head of a locking screw, and the second through hole comprising non-threaded first and second regions;
    inserting a compression screw through the second through hole and into engagement with bone such that the non-threaded head of the compression screw contacts the non-threaded first region of the second through hole to move the bone plate in a desired direction relative to the bone to provide axial compression of the bone fracture; and
    inserting a locking screw through the first through hole and into engagement with bone such that the threaded head of the locking screw engages the second region of the through hole to maintain fixation of the bone plate relative to the bone.

15. The method of claim 14, further comprising adjusting the position of the bone and surrounding tissue by adjusting the insertion of the compression screw by up to about two millimeters in more than one direction.

16. The method of claim 14, further comprising inserting the compression screw through the through hole such that the non-threaded head of the compression screw contacts the first region and rides along the first region allowing for adjustment of up to about two millimeters in a desired direction.

17. The method of claim 14, further comprising inserting one or more provisional fixation pins through the bone plate and into engagement with the bone.

18. The method of claim 17, further comprising adjusting the one or more provisional fixation pins to draw a bone fragment to the bone plate.

* * * * *